United States Patent [19]
Brewer et al.

[11] Patent Number: 5,908,443
[45] Date of Patent: *Jun. 1, 1999

[54] STACKED CAPACITOR TRUNCATED DAMPED SINUSOIDAL DEFIBRILLATION WAVEFORM

[75] Inventors: James E. Brewer, Cottage Grove; Gary B. Stendahl, Crystal, both of Minn.

[73] Assignee: SurVivaLink Corporation, Minneapolis, Minn.

[21] Appl. No.: 08/827,757

[22] Filed: Apr. 11, 1997

Related U.S. Application Data

[60] Provisional application No. 60/015,343, Apr. 12, 1996.
[51] Int. Cl.$^6$ ................................................ A61N 1/390
[52] U.S. Cl. ................................ 607/8; 607/5; 607/68; 607/74
[58] Field of Search ................................ 607/5, 7, 8, 68, 607/70, 74, 76

[56] References Cited

U.S. PATENT DOCUMENTS

| | | | |
|---|---|---|---|
| 3,886,950 | 6/1975 | Ukkestad et al. ............................ | 607/5 |
| 4,637,397 | 1/1987 | Jones et al. ................................. | 607/5 |
| 4,768,512 | 9/1988 | Imran . | |
| 5,350,403 | 9/1994 | Stroetmann et al. ....................... | 607/8 |
| 5,391,186 | 2/1995 | Kroll et al. . | |
| 5,431,686 | 7/1995 | Kroll et al. . | |
| 5,507,781 | 4/1996 | Kroll et al. ................................ | 607/5 |
| 5,591,209 | 1/1997 | Kroll ......................................... | 607/5 |
| 5,593,427 | 1/1997 | Gilner et al. . | |
| 5,601,612 | 2/1997 | Gilner et al. . | |
| 5,607,454 | 3/1997 | Cameron et al. . | |

FOREIGN PATENT DOCUMENTS

| | | |
|---|---|---|
| WO 95/09673 | 4/1995 | WIPO . |
| WO 95/32020 | 11/1995 | WIPO . |

*Primary Examiner*—William E. Kamm
*Assistant Examiner*—George R. Evanisko
*Attorney, Agent, or Firm*—Patterson & Keough, P.A.

[57] ABSTRACT

An apparatus for generating a waveform for use in externally defibrillating the heart of a patient includes a plurality of capacitors chargeable to respective charge potentials. A control apparatus is operatively coupled with the capacitors to sequentially interconnect the capacitors in a circuit with one another to generate the waveform. Structure including e.g. electrodes is operatively coupled with the capacitors and the control apparatus to apply the waveform to the chest of the patient. The waveform preferably includes an emulated first-phase substantially sinusoidally shaped pulse component having a first polarity. According to biphasic embodiments, the waveform also includes an emulated second-phase substantially sinusoidally shaped pulse component having a second polarity. The control apparatus preferably is constructed to truncate the emulated first-phase pulse component at a predetermined time, preferably based on a design rule used to calculate pulse duration. The design rule calculates the pulse duration to correspond to substantially the peak response of the patient's heart-cell membrane to the first-phase pulse component. Corresponding method embodiments provide additional advantages.

22 Claims, 26 Drawing Sheets

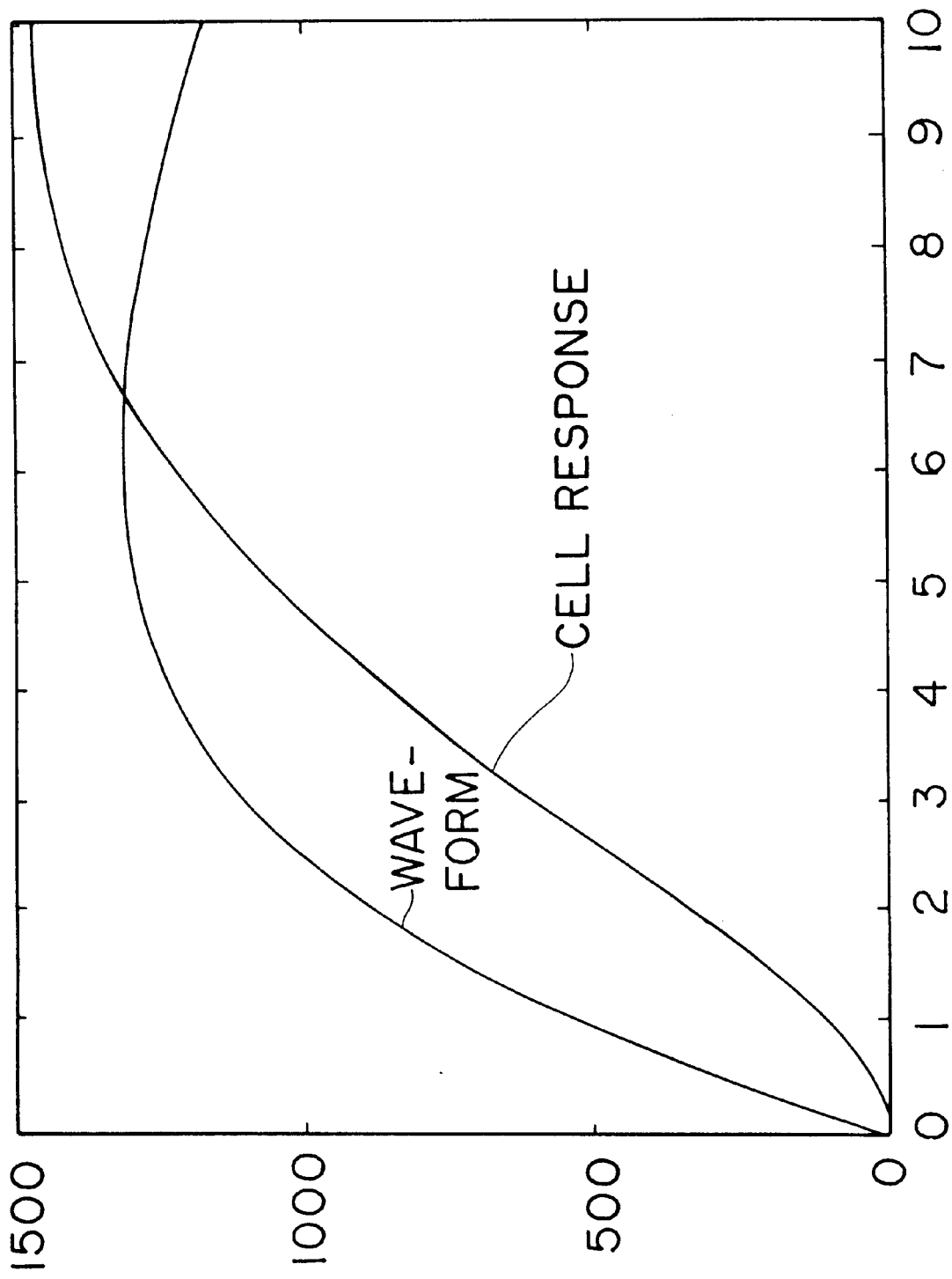

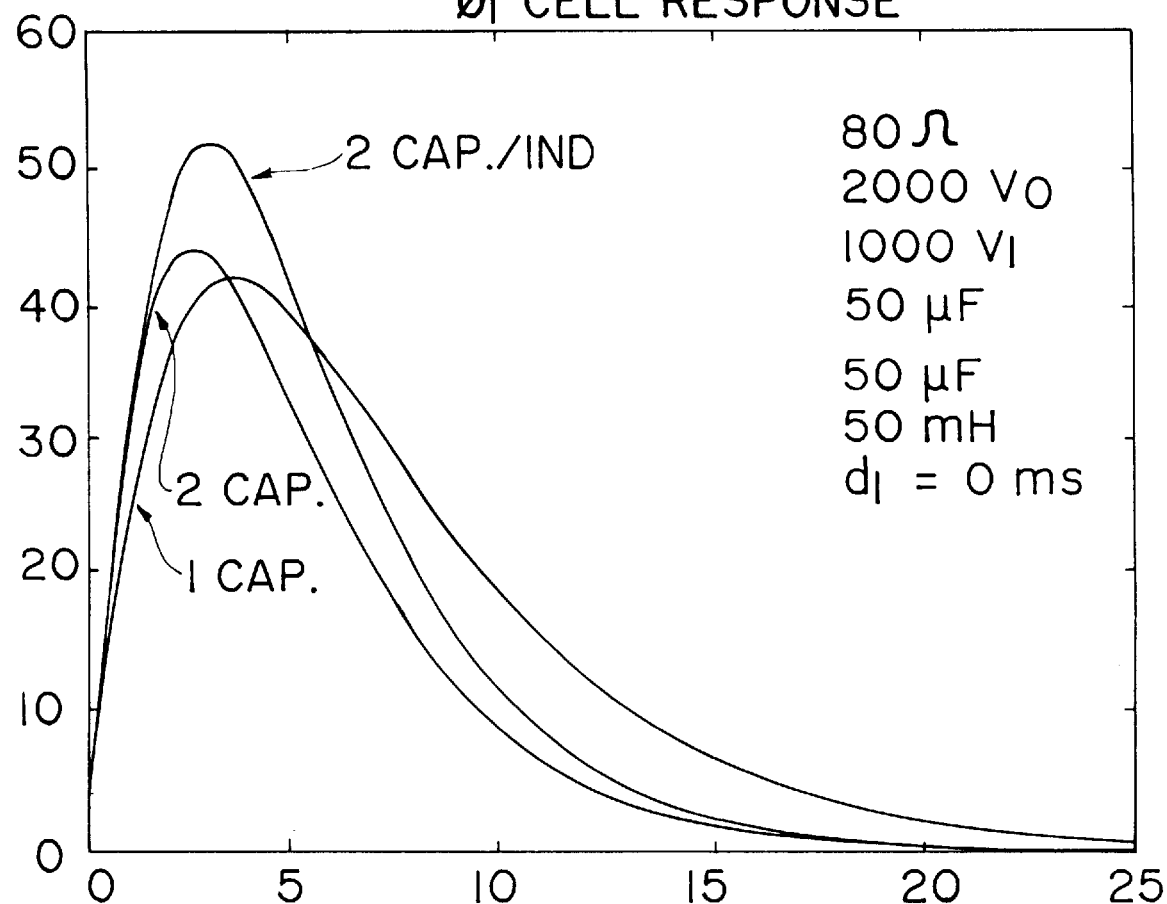

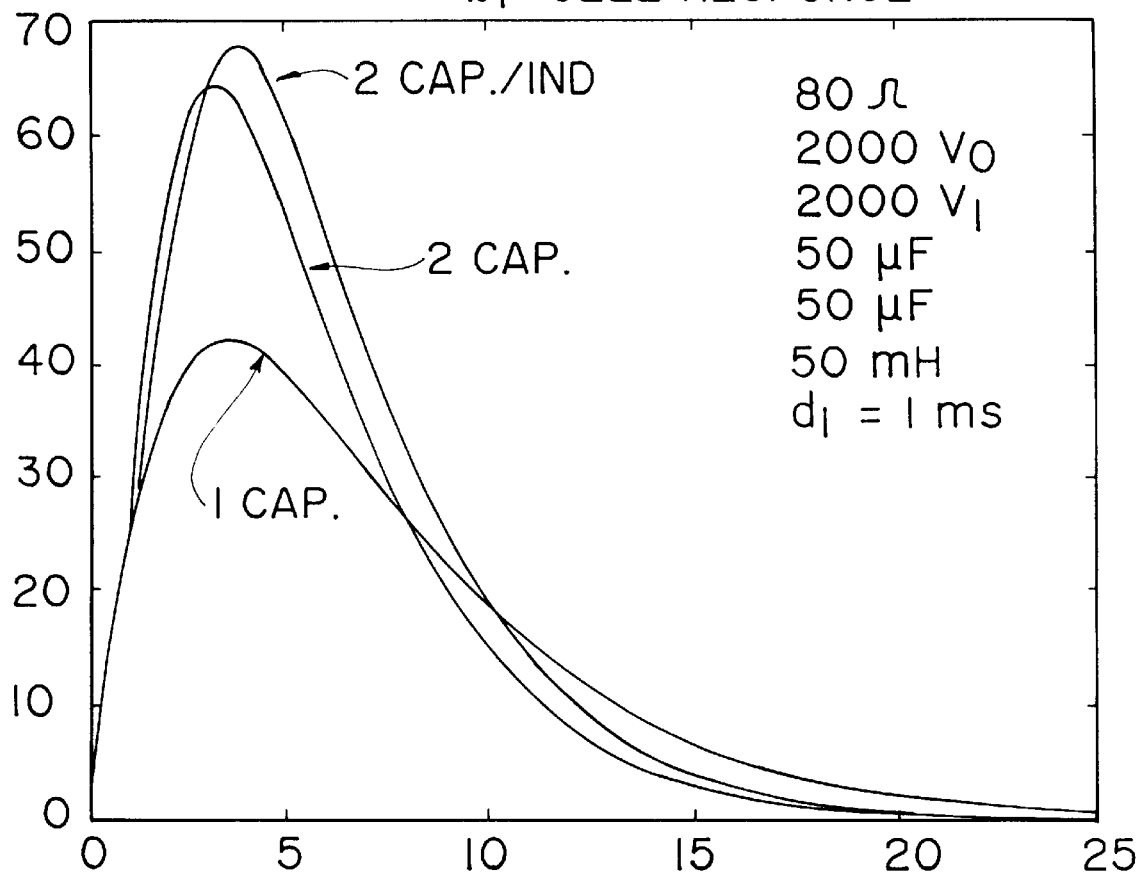

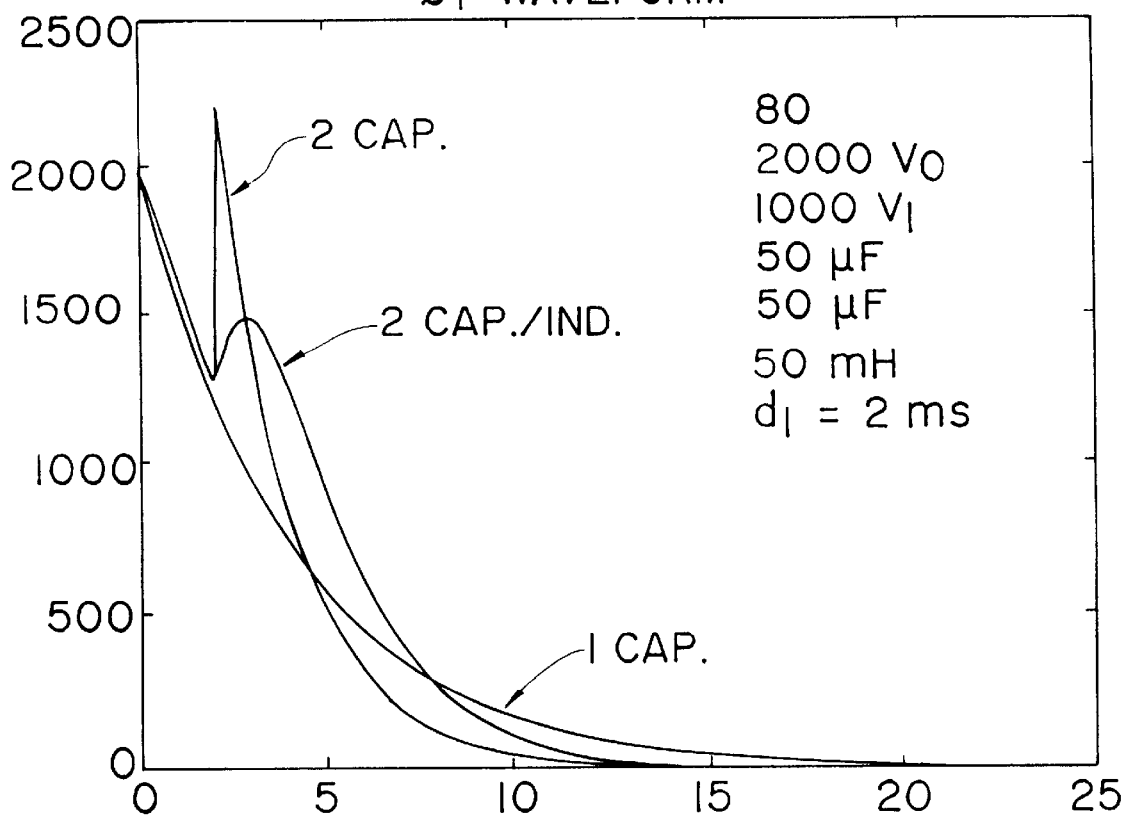

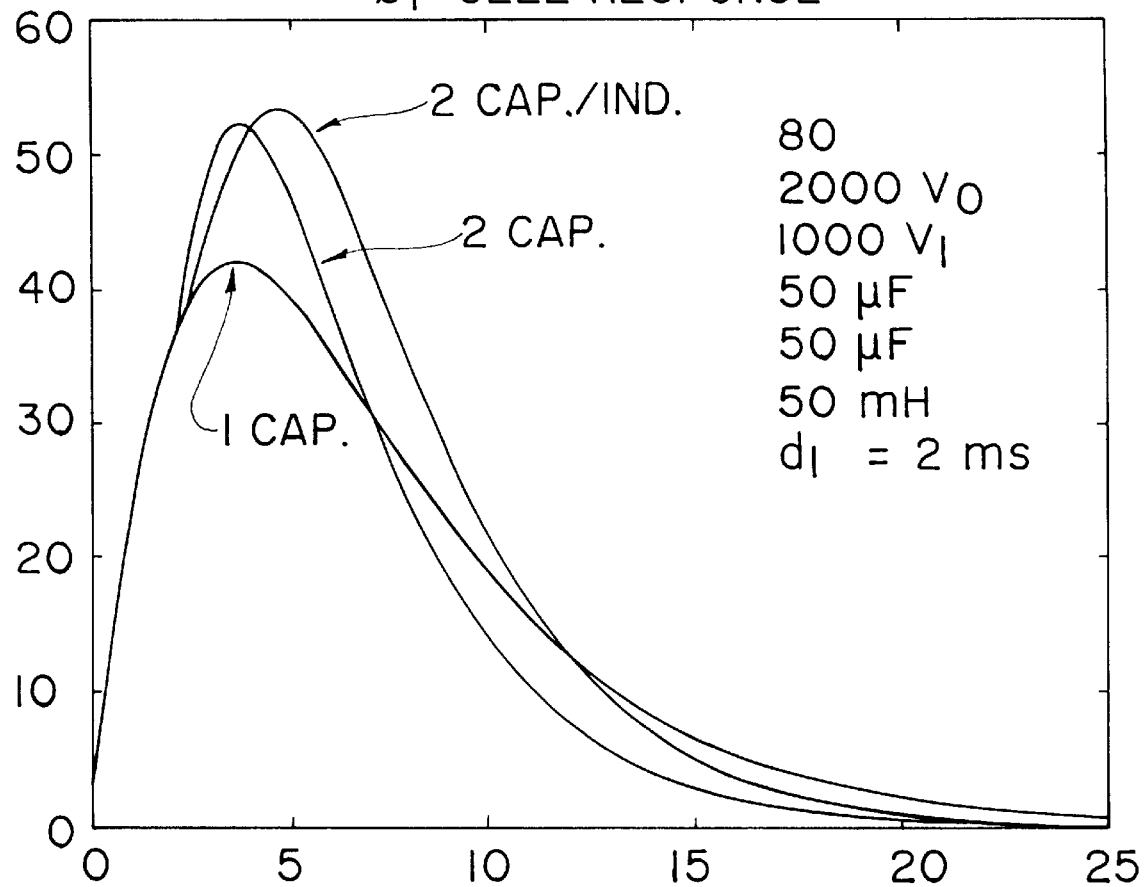

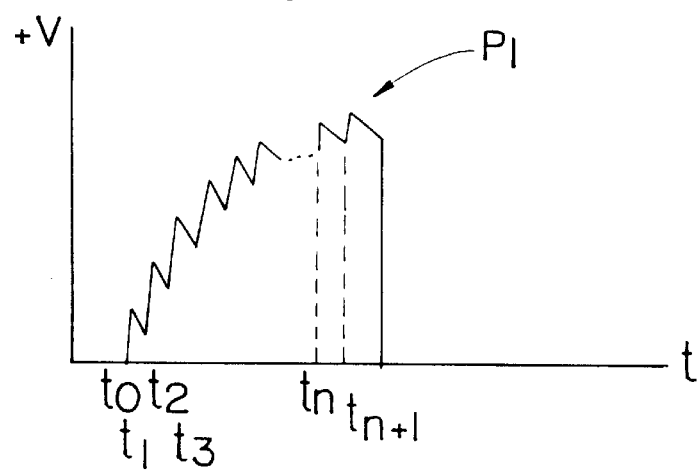
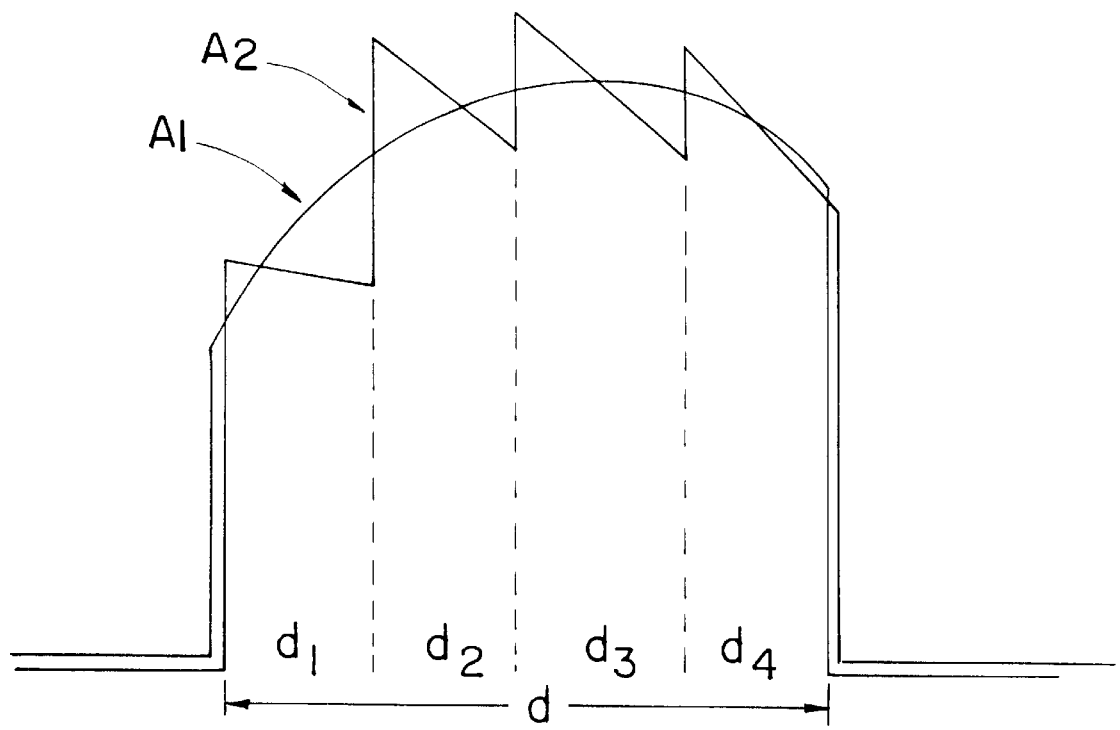

$d_1$ = FIRST DELIVER PULSE
$d_2$ = SECOND DELIVER PULSE
$d_n$ = $n^{th}$ DELIVER PULSE

STACKED CAPACITOR TRUNCATED DAMPED SINUSOIDAL DEFIBRILLATION WAVEFORM

RELATED APPLICATIONS

This application is based on provisional patent application Serial No. 60/015,343, filed Apr. 12, 1996 entitled METHOD OF DESIGNING EXTERNAL DEFIBRILLATOR WAVEFORMS, the contents of which are herein incorporated by reference and priority back to the Apr. 12, 1996 filing date is hereby claimed.

FIELD OF THE INVENTION

This invention relates generally to an electrotherapy method and apparatus for delivering an electrical pulse to a patient's heart. In particular, this invention relates to a method and apparatus for creating an emulated truncated sinusoidal electrical waveform delivered by an external defibrillator based on theory and practice as described herein.

BACKGROUND OF THE INVENTION

Devices for defibrillating a heart have been known for some time now. Implantable defibrillators are well-accepted by the medical community as effective tools to combat fibrillation for an identified segment of the population. A substantial amount of research in fibrillation and the therapy of defibrillation has been done. Much of the most recent research has concentrated on understanding the effects that a defibrillation shock pulse has on fibrillation to terminate such a condition.

A monophasic waveform is defined to be a single phase, capacitive-discharge, time-truncated, waveform with exponential decay. A biphasic waveform is defined to comprise two monophasic waveforms, separated by time and of opposite polarity. The first phase is designated $\phi_1$ and the second phase is designated $\phi_2$. The delivery of $\phi_1$ is completed before the delivery of $\phi_2$ is begun.

After extensive testing, it has been determined that biphasic waveforms are more efficacious than monophasic waveforms. There is a wide debate regarding the reasons for the increased efficacy of biphasic waveforms over that of a monophasic waveforms. One hypothesis holds that $\phi_1$ defibrillates the heart and $\phi_2$ performs a stabilizing action that keeps the heart from refibrillating.

Biphasic defibrillation waveforms are now the standard of care in clinical use for defibrillation with implantable cardioverter-defibrillators (ICDs), due to the superior performance demonstrated over that of comparable monophasic waveforms. To better understand these significantly different outcomes, ICD research has developed cardiac cell response models to defibrillation. Waveform design criteria have been derived from these first principles and have been applied to monophasic and biphasic waveforms to optimize their parameters. These principles-based design criteria have produced significant improvements over the current art of waveforms.

In a two paper set, Blair developed a model for the optimal design of a monophasic waveform when used for electrical stimulation. (1) Blair, H. A., "On the Intensity-time relations for stimulation by electric currents." I. J. Gen. Physiol. 1932; 15: 709–729. (2) Blair, H. A., "On the Intensity-time Relations for stimulation by electric currents." II. J. Gen. Physiol. 1932; 15: 731–755. Blair proposed and demonstrated that the optimal duration of a monophasic waveform is equal to the point in time at which the cell response to the stimulus is maximal. Duplicating Blair's model, Walcott extended Blair's analysis to defibrillation, where they obtained supporting experimental results. Walcott, et al., "Choosing the optimal monophasic and biphasic waveforms for ventricular defibrillation." J. Cardiovasc Electrophysiol. 1995; 6: 737–750.

Independently, Kroll developed a biphasic model for the optimal design of $\phi_2$ for a biphasic defibrillation waveform. Kroll, M. W., "A minimal model of the single capacitor biphasic defibrillation waveform." PACE 1994; 17:1782–1792. Kroll proposed that the $\phi_2$ stabilizing action removed the charge deposited by $\phi_1$ from those cells not stimulated by $\phi_1$. This has come to be known as "charge burping". Kroll supported his hypothesis with retrospective analysis of studies by Dixon, et al., Tang, et al., and Freese, et al. regarding single capacitor, biphasic waveform studies. Dixon, et al., "Improved defibrillation thresholds with large contoured epicardial electrodes and biphasic waveforms." Circulation 1987; 76:1176–1184; Tang, et al. "Ventricular defibrillation using biphasic waveforms: The Importance of Phasic duration." J. Am. Coll. Cardiol. 1989; 13:207–214; and Feeser, S. A., et al. "Strength-duration and probability of success curves for defibrillation with biphasic waveforms." Circulation 1990; 82: 2128–2141. Again, the Walcott group retrospectively evaluated their extension of Blair's model to $\phi_2$ using the Tang and Feeser data sets. Their findings further supported Kroll's hypothesis regarding biphasic defibrillation waveforms. For further discussions on the development of these models, reference may be made to PCT publications WO 95/32020 and WO 95/09673 and to U.S. Pat. No. 5,431,686.

The charge burping hypothesis can be used to develop equations that describe the time course of a cell's membrane potential during a biphasic shock pulse. At the end of $\phi_1$, those cells that were not stimulated by $\phi_1$ have a residual charge due to the action of $\phi_1$ on the cell. The charge burping model hypothesizes that an optimal pulse duration for $\phi_2$ is that duration that removes as much of the $\phi_1$ residual charge from the cell as possible. Ideally, these unstimulated cells are set back to "relative ground." The charge burping model proposed by Kroll is based on the circuit model shown in FIG. 2b which is adapted from the general model of a defibrillator illustrated in FIG. 2a.

The charge burping model also accounts for removing the residual cell membrane potential at the end of a $\phi_1$ pulse that is independent of a $\phi_2$. That is, $\phi_2$ is delivered by a set of capacitors separate from the set of capacitors used to deliver $\phi_1$. This charge burping model is constructed by adding a second set of capacitors, as illustrated in FIG. 3. In this figure, $C_1$ represents the $\phi_1$ capacitor set, $C_2$ represents the $\phi_2$ capacitor set $R_H$ represents the resistance of the heart, and the pair $C_M$ and $R_M$ represent membrane series capacitance and resistance of a single cell. The node $V_s$ represents the voltage between the electrodes, while $V_M$ denotes the voltage across the cell membrane.

External defibrillators send electrical pulses to the patient's heart through electrodes applied to the patient's torso. External defibrillators are useful in any situation where there may be an unanticipated need to provide electrotherapy to a patient on short notice. The advantage of external defibrillators is that they may be used on a patient as needed, then subsequently moved to be used with another patient.

However, this important advantage has two fundamental limitations. First, external defibrillators do not have direct contact with the patient's heart. External defibrillators have traditionally delivered their electrotherapeutic pulses to the patient's heart from the surface of the patient's chest. This is known as the transthoracic defibrillation problem. Second, external defibrillators must be able to be used on patients having a variety of physiological differences. External defibrillators have traditionally operated according to pulse amplitude and duration parameters that can be effective in all patients. This is known as the patient variability problem.

The prior art described above effectively models implantable defibrillators, however it does not fully addressed the transthoracic defibrillation problem nor the patient variability problem. In fact, these two limitations to external defibrillators are not fully appreciated by those in the art. For example, prior art disclosures of the use of truncated monophasic or biphasic shock pulses in implantable or external defibrillators have provided little guidance for the design of an external defibrillator that will successfully defibrillate across a large, heterogeneous population of patients. In particular, an implantable defibrillator and an external defibrillator can deliver a shock pulse of similar form, and yet the actual implementation of the waveform delivery system is radically different.

In the past five years, new research in ICD therapy has developed and demonstrated defibrillation models that provide waveform design rules from first principles. These defibrillation models and their associated design rules for the development of defibrillation waveforms and their characteristics were first developed by Kroll and Irnich for monophasic waveforms using effective and rheobase current concepts. (1) Kroll, M. W., "A minimal model of the monophasic defibrillation pulse." PACE 1993; 15: 769. (2) Irnich, W., "Optimal truncation of defibrillation pulses." PACE 1995; 18: 673. Subsequently, Kroll, Walcott, Cleland and others developed the passive cardiac cell membrane response model for monophasic and biphasic waveforms, herein called the cell response model. (1) Kroll, M. W., "A minimal model of the single capacitor biphasic defibrillation waveform." PACE 1994; 17: 1782. (2) Walcott, G. P., Walker, R. G., Cates. A. W., Krassowska, W., Smith, W. M., Ideker R. E. "Choosing the optimal monophasic and biphasic waveforms for ventricular defibrillation." J Cardiovasc Electrophysiol 1995; 6:737; and Cleland B. G. "A conceptual basis for defibrillation waveforms." PACE 1996; 19:1186.

A significant increase in the understanding of waveform design has occurred and substantial improvements have been made by using these newly developed design principles. Block et al. has recently written a comprehensive survey of the new principles-based theories and their impact on optimizing internal defibrillation through improved waveforms. Block M., Breithardt G., "Optimizing defibrillation through improved waveforms." PACE 1995; 18:526.

There have not been significant developments in external defibrillation waveforms beyond the two basic monophasic waveforms: the damped sine or the truncated exponential. To date, their design for transthoracic defibrillation has been based almost entirely on empirically derived data. It seems that the design of monophasic and biphasic waveforms for external defibrillation has not yet been generally influenced by the important developments in ICD research.

Recently there has been reported research on the development and validation of a biphasic truncated exponential waveform in which it was compared clinically to a damped sine waveform. For additional background, reference may be made to U.S. Pat. Nos. 5,593,427, 5,601,612 and 5,607,454. See also: Gliner B. E., Lyster T. E., Dillon S. M., Bardy G. H., "Transthoracic defibrillation of swine with monophasic and biphasic waveforms." Circulation 1995; 92:1634–1643; Bardy G. H., Gliner B. E., Kudenchuk P. J., Poole J. E., Dolack G. L., Jones G. K., Anderson J., Troutman C., Johnson G.; "Truncated biphasic pulses for transthoracic defibrillation." Circulation 1995; 91:1768–1774; and Bardy G. H. et al, "For the Transthoracic Investigators. Multicenter comparison of truncated biphasic shocks and standard damped sine wave monophasic shocks for transthoracic ventricular defibrillation." Circulation 1996; 94:2507–2514. Although the research determined a usable biphasic waveform, there was no new theoretical understanding determined for external waveform design. It appears that external waveform research may develop a "rules-of-thumb by trial and error" design approach much like that established in the early stages of theoretical ICD research. The noted limitations of the transthoracic biphasic waveform may be due in part to a lack of principles-based design rules to determine its waveform characteristics.

Monophasic defibrillation waveforms remain the standard of care in clinical use for transthoracic defibrillation. Waveform design has not yet been influenced by the important gains made in ICD research. The limitations of present transthoracic waveforms may be due in part to a lack of application of these design principles to determine optimal waveform characteristics. To overcome these limitations, design principles and design rules based on cell response have recently been developed for external defibrillation waveforms. The transthoracic model incorporates elements into a cell response model that extends it to external defibrillation.

Damped sine waves have been used and are well known to those skilled in the art of defibrillators for some time now. Known circuits for developing damped sine waveforms typically have a very large leading edge voltage which is damped by the inductor. Due to rapid rise time, the known damped sine waveform implementations do not track the cell membrane response. By incorporating a larger inductor (25 mH–500 mH) and by truncating each phase of the delivery of the damped sine waveform at appropriate times defined by design rules based on a desired cardiac cell response, damped sine waveforms can better track cell membrane response, thereby providing a more effective defibrillation shock pulse.

It is known that constant current pulses, such as square waves or rectangular waves are the most effective waveforms for defibrillation. Schuder J. C. et al., "Transthoracic Ventricular Defibrillation of 100 Kilogram Calves with Critically Damped Sinusoidal Shocks." AAMI 21st Annual Meeting, Apr. 12–16, 1986. However, generally a constant current waveform has proven costly and size prohibitive.

There is a continued need for an apparatus and method for accurately delivering an external defibrillator waveform to efficiently and effectively provide a desired response in the patient cardiac cell membrane. Additionally, there is a need for a method and apparatus for approximating a constant current waveform.

SUMMARY OF THE INVENTION

The present invention relates to an external defibrillation method and apparatus that addresses the limitations in the prior art. The present invention incorporates three singular practices that distinguish the practice of designing external defibrillators from the practice of designing implantable defibrillators. These practices are 1) designing multiphasic transthoracic shock pulse waveforms from principles based on cardiac electrophysiology, 2) designing multiphasic transthoracic shock pulse waveforms in which each phase of the waveform can be designed without implementation limitations placed on its charging and delivery means by such means for prior waveform phases, and 3) designing multiphasic transthoracic shock pulse waveforms to operate across a wide range of parameters determined by a large, heterogeneous population of patients.

In particular, the present invention provides a method and apparatus for generating a waveform for use in externally defibrillating the heart of a patient, including use of a plurality of capacitors chargeable to respective charge potentials. A control apparatus is operatively coupled with the capacitors to sequentially interconnect the capacitors in a circuit with one another to generate the waveform. Structure including e.g. electrodes can be operatively coupled with the capacitors and the control apparatus to apply the waveform to the chest of the patient.

According to embodiments of the invention, the waveform comprises an emulated first-phase substantially sinusoidally shaped pulse component having a first polarity. According to biphasic embodiments, the waveform also includes an emulated second-phase substantially sinusoidally shaped pulse component having a second polarity. The control apparatus preferably is constructed to truncate the emulated first-phase pulse component at a predetermined time, preferably based on a design rule used to calculate pulse duration. The design rule calculates the pulse duration to correspond to substantially the peak response of the patient's heart-cell membrane to the first-phase pulse component.

These and other aspects of the invention will become apparent from the remainder of the application.

BRIEF DESCRIPTION OF THE DRAWINGS

FIGS. 8a, 8b and 8c are illustrations of single capacitor damped sinusoidal waveforms and associated cell membrane responses.

FIGS. 15a, 15b, 15c, 15d, 15e, and 15f illustrate a plurality of waveforms and their associated cell responses with a variety of parameters.

FIG. 16B shows a stepped waveform according to an embodiment of the invention.

FIG. 17A shows a stepped waveform according to an embodiment of the invention.

DETAILED DESCRIPTION OF PREFERRED EMBODIMENTS

The present invention provides a method and apparatus for delivering an emulated external defibrillation waveform which, when applied through a plurality of electrodes positioned on a patient's torso, will provide a desired response in the patient's cardiac cell membrane. To better understand the present invention, a discussion of the development of an appropriate model will first be presented.

Description of External Defibrillation Model

Figure 1A:
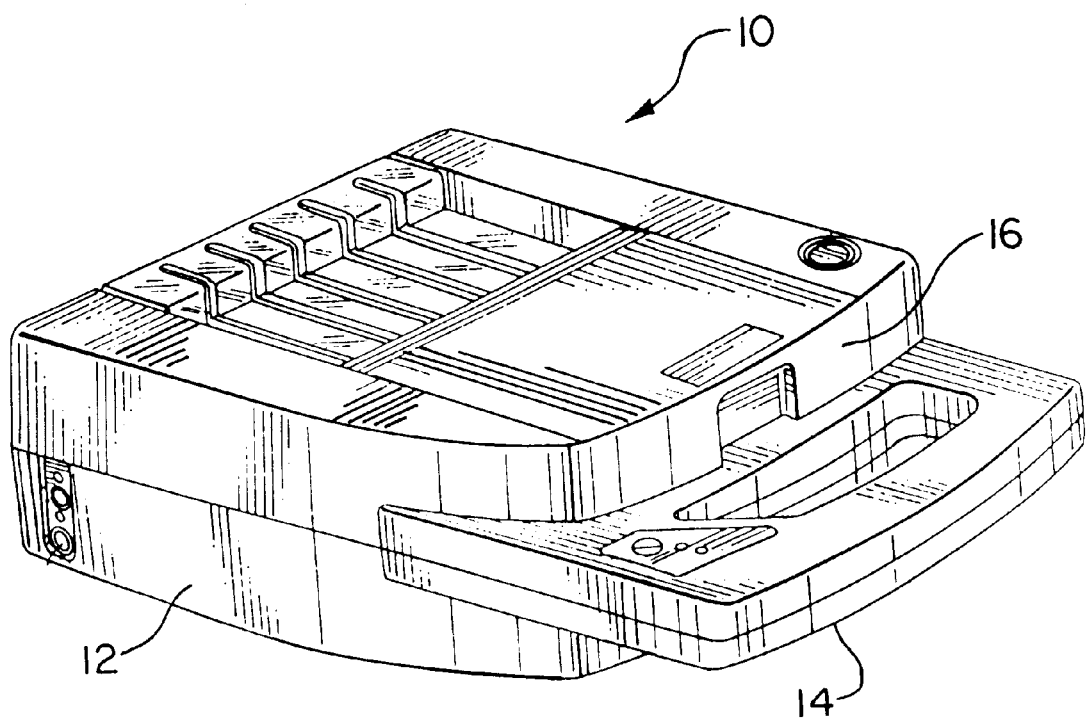
FIGS. 1a and 1b are perspective views of an AED according to embodiments of the invention.
Figure 1B:
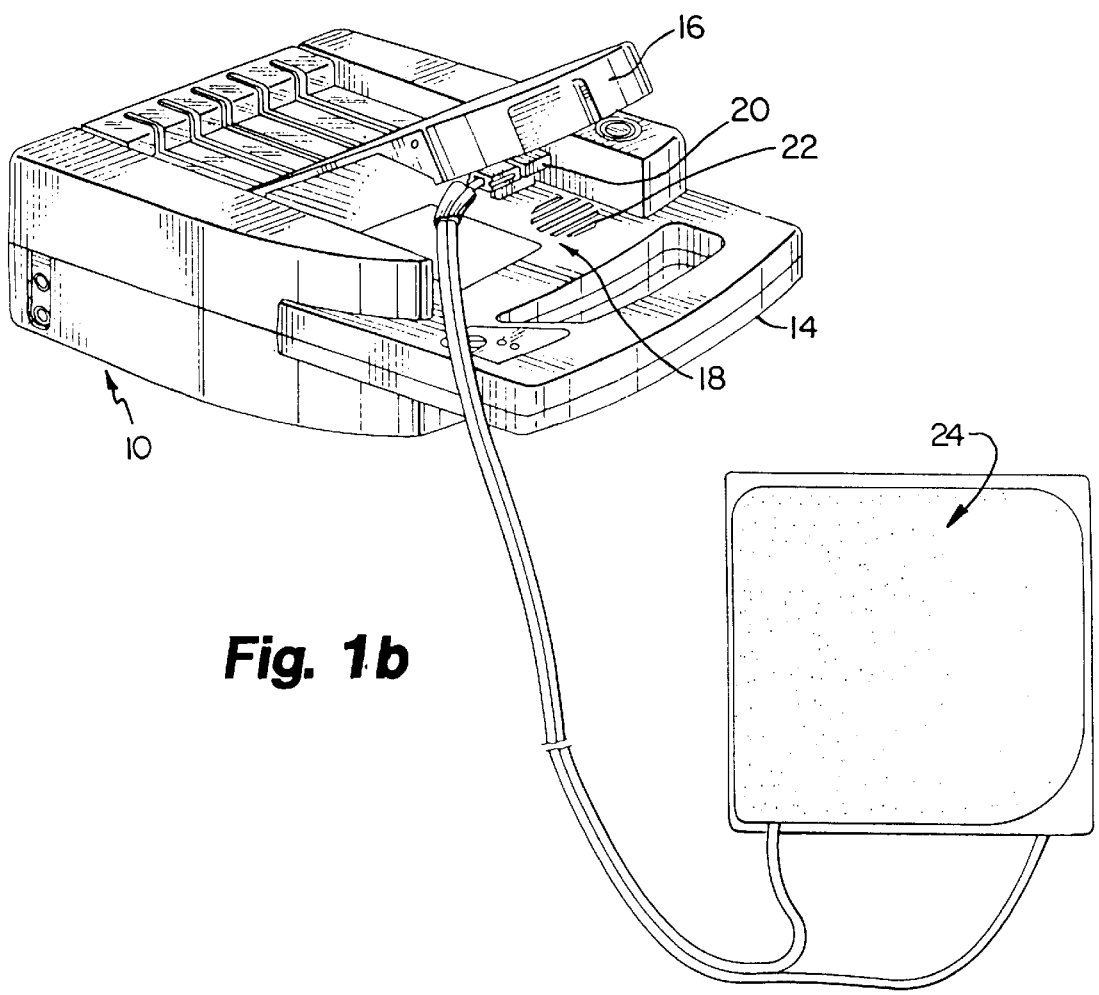

An automated external defibrillator (AED) is illustrated in FIGS. 1a and 1b. FIG. 1a illustrates an AED 10, including a plastic case 12 with a carrying handle 14. A lid 16 is provided which covers an electrode compartment 18. An electrode connector 20, a speaker 22 and a diagnostic panel (not shown) are located on case 12 within electrode compartment 18. FIG. 1b illustrates AED 10 having a pair of electrodes 24 connected thereto. Electrodes 24 can be pre-connected to connector 20 and stored in compartment 18.

The operation of AED 10 is described briefly below. A rescue mode of AED 10 is initiated when lid 16 is opened to access electrodes 24. The opening of lid 16 is detected by AED 10 to effectively turn on the device. AED 10 then quickly runs a short test routine. After electrodes 24 have been placed on the patient, AED 10 senses patient specific parameters, such as voltage, current, charge or other measurable parameters of the patient. The patient specific parameters are then utilized in the design of optimal waveforms as will be described below.

If a shockable condition is detected through electrodes 24, a plurality of capacitors inside of AED 10 are charged from an energy source, typically a detachable battery pack. Based upon the patient specific parameters sensed, the duration and other characteristics of a discharge waveform are then calculated. The energy stored in AED 10 is then discharged to the patient through electrodes 24.

For a more detailed description of the physical structure of AED 10 or the process involved in sensing, charging, shocking and testing, reference should be made to applicants co-pending application Ser. No. 08/512,441 now U.S. Pat. No. 5,645,571, filed Aug. 8, 1995 entitled AUTOMATED EXTERNAL DEFIBRILLATOR WITH SELF-TEST SYSTEM which is assigned to the assignee of the present invention, the disclosure of which is herein incorporated by reference.

It is not assumed that both phases of a biphasic waveform are delivered using the same set of capacitors or that both phases of a biphasic waveform are delivered using the capacitor set in the same electrical configuration, although such an embodiment is considered within the spirit and scope of the present invention.

Transthoracic defibrillation is generally performed by placing electrodes on the apex and anterior positions of the chest wall. With this electrode arrangement, nearly all current passing through the heart is conducted by the lungs and the equipotential surfaces pass through the myocardium normal to the electrode axis. The transthoracic charge burping model is used to develop design equations that describe the time course of a cell's membrane potential during a transthoracic biphasic shock pulse. These equations are then used to create equations that describe the design of monophasic and biphasic shock pulses for trans chest defibrillation to optimize the design of $\phi_1$ for defibrillating and the design of $\phi_2$ for stabilizing. These optimizing shock pulse design equations are called design rules.

The main series pathway for current is to pass through the chest wall, the lungs, and the heart. Additionally, there are two important shunting pathways in parallel with the current pathway through the heart. These shunting pathways must be taken into consideration. The lungs shunt current around the heart through a parallel pathway. The second shunting pathway is provided by the thoracic cage. The resistivity of the thoracic cage and the skeletal muscle structure is low when compared to lungs. The high resistivity of the lungs and the shunting pathways are characterizing elements of external defibrillation that distinguish the art from intracardiac defibrillation and implantable defibrillation technologies.

Figure 4:
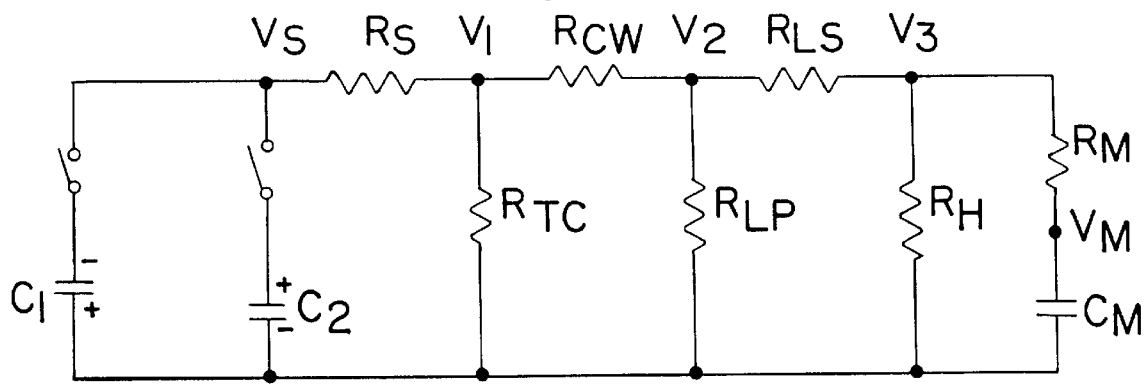
FIG. 4 represents a monophasic or biphasic capacitive-discharge external defibrillation model according to the invention.

Therefore, in the transthoracic defibrillation model illustrated in FIG. 4, there are several resistances in addition to those discussed for the charge burping model above. $R_S$ represents the resistance of the defibrillation system, including the resistance of the defibrillation electrodes. $R_{CW}$ and $R_{LS}$ represent the resistances of the chest wall and the lungs, respectively, in series with resistance of the heart, $R_H$. $R_{TC}$ and $R_{LP}$ represent the resistances of the thoracic cage and the lungs, respectively, in parallel with the resistance of the heart.

The design rules for external defibrillation waveforms are determined in three steps. In the first step, the transchest forcing function is determined. The transchest forcing function is the name that is given to the voltage that is applied across each cardiac cell during an external defibrillation shock. In the second step, the design equations for $\phi_1$ of a shock pulse are determined. The design equations are the equations describing the cell's response to the $\phi_1$ transchest forcing function, the equation describing the optimal $\phi_1$ pulse duration, and the equation describing the optimal $\phi_1$ capacitor. Therefore, step two relates the cell response to the action of a monophasic shock pulse or the first phase of a biphasic shock pulse. This relation is used to determine the optimal design rules and thereby design parameters for the implementation of this phase in an external defibrillator. It will be clear to those in the art that step two is not restricted to capacitor discharge shock pulses and their associated transchest forcing function. Another common implementation of an external defibrillator incorporates a damped sine wave for a shock pulse and can be either a monophasic or biphasic waveform. This type of external defibrillator is modeled by the circuit shown in FIG. 5. In the third step, the design equations for $\phi_2$ of a shock pulse are determined. The design equations are the equations describing the cell's response to the $\phi_2$ transchest forcing function, the equation describing the optimal $\phi_2$ pulse duration and the equation describing the optimal $\phi_2$ capacitor. These design equations are employed to determine the optimal design rules and thereby design parameters of $\phi_2$ of a biphasic shock pulse with respect to how the cell responds to the shock pulse. An important element of this invention is to provide shock pulse waveforms that are designed from a cardiac cell response model developed from first principles and that correctly determines the effects of the chest and its components on the ability of a shock pulse to defibrillate.

The transchest forcing function is determined by solving for the voltage found at node $V_3$ in FIG. 4. The transchest forcing function is derived by solving for $V_3$ using the following three nodal equations:

$$\frac{V_1 - V_S}{R_S} + \frac{V_1}{R_{TC}} + \frac{V_1 - V_2}{R_{CW}} = 0, \quad (1)$$

$$\frac{V_2 - V_1}{R_{CW}} + \frac{V_2}{R_{LP}} + \frac{V_2 - V_3}{R_{LS}} = 0, \quad (2)$$

and $$\frac{V_3 - V_2}{R_{LS}} + \frac{V_3}{R_H} + \frac{V_3 - V_M}{R_M} = 0. \quad (3)$$

Equation 1 can be rewritten as $$V_1\left(\frac{1}{R_S} + \frac{1}{R_{TC}} + \frac{1}{R_{CW}}\right) = \frac{V_S}{R_S} + \frac{V_2}{R_{CW}}. \quad (4A)$$

$$V_1 = \frac{V_S}{R_S \Omega_1} + \frac{V_2}{R_{CW} \Omega_1}, \quad (4B)$$

where $$\Omega_1 = \frac{1}{R_S} + \frac{1}{R_{TC}} + \frac{1}{R_{CW}}.$$

Rewriting equation 2, we have $$V_2\left(\frac{1}{R_{CW}} + \frac{1}{R_{LP}} + \frac{1}{R_{LS}}\right) = \frac{V_1}{R_{CW}} + \frac{V_3}{R_{LS}}. \quad (4C)$$

By substituting equation 4B for $V_1$ into equation 4C, we can solve for $V_2$ as an expression of $V_S$ and $V_3$:

$$V_2 = \frac{V_S}{R_S R_{CW} \Omega_1 \Omega_2 \Omega_{22}} + \frac{V_3}{R_{LS} \Omega_2 \Omega_{22}}, \quad (5)$$

where $$\Omega_2 = \frac{1}{R_{LS}} + \frac{1}{R_{LP}} + \frac{1}{R_{CW}},$$

and $$\Omega_{22} = 1 - \frac{1}{R_{CW}^2 \Omega_1 \Omega_2}.$$

Now solving for $V_3$ as an expression of $V_S$ and $V_M$, equation 3 may be re-arranged as $$V_3 \left( \frac{1}{R_{LS}} + \frac{1}{R_H} + \frac{1}{R_M} \right) = \frac{V_2}{R_{LS}} + \frac{V_M}{R_M} \quad (6)$$

so that $$V_3 = \frac{V_2}{R_{LS} \Omega_3} + \frac{V_M}{R_M \Omega_3} \quad (7)$$

where $$\Omega_3 = \frac{1}{R_{LS}} + \frac{1}{R_H} + \frac{1}{R_M}.$$

Substituting equation 5 for $V_2$ into equation 7, we can solve for $V_3$ as an expression of $V_S$ and $V_M$:

$$V_3 = \frac{V_S}{R_S R_{CW} R_{LS} \Omega_1 \Omega_2 \Omega_{22} \Omega_3 \Omega_{33}} + \frac{V_M}{R_M \Omega_3 \Omega_{33}} \quad (8)$$

where $$\Omega_{33} = 1 - \frac{1}{(R_{LS}^2 \Omega_2 \Omega_{22} \Omega_3)} \quad (9)$$

From equation 8 we define $\Omega_M$ to be:

$$\Omega_M = R_M \Omega_3 \Omega_{33} = R_M \Omega_3 \left( 1 - \frac{1}{(R_{LS}^2 \Omega_2 \Omega_{22} \Omega_3)} \right) \quad (10)$$

$$\Omega_M = R_M \left( \Omega_3 - \frac{1}{R_{LS}^2 \left( \Omega_2 - \frac{1}{R_{CW}^2 \Omega_1} \right)} \right)$$

Figure 5A:
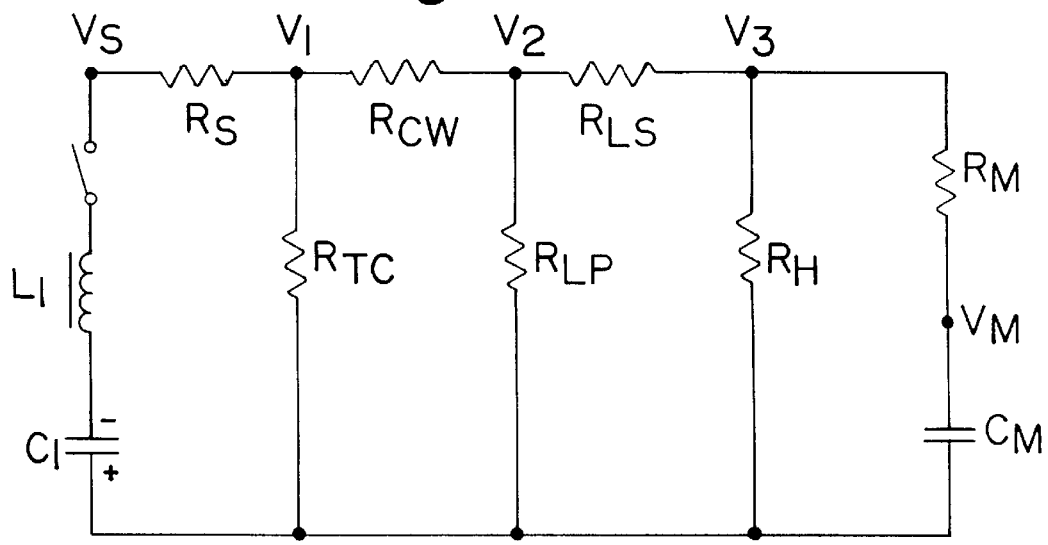
FIG. 5a represents a monophasic capacitor-inductor external defibrillator model according to the invention.
Figure 5B:
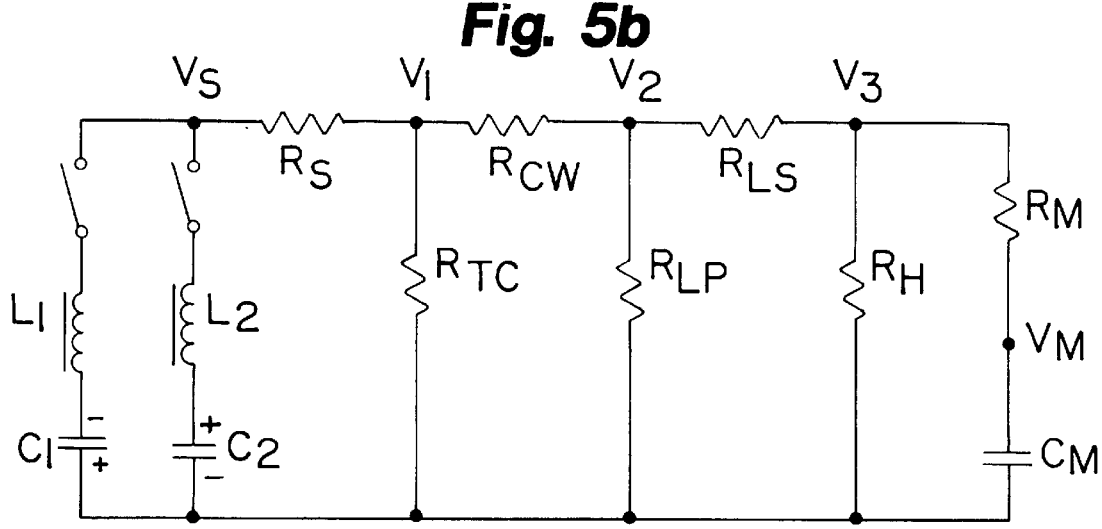
FIG. 5b represents an alternative embodiment of a biphasic capacitor-inductor external defibrillator model according to the invention.

From equation 8 we also define $\Omega_S$ to be:

$$\Omega_S = R_S R_{CW} R_{LS} \Omega_1 \Omega_2 \Omega_3 \Omega_{22} \Omega_{33} \quad (11)$$

$$\Omega_S = R_S R_{CW} R_{LS} \Omega_1 \Omega_2 \left( 1 - \frac{1}{(R_{CW}^2 \Omega_1 \Omega_2)} \right) \Omega_3 \left( 1 - \frac{1}{(R_{LS}^2 \Omega_2 \Omega_{22} \Omega_3)} \right) \quad (12)$$

$$\Omega_S = R_S R_{CW} R_{LS} \left( \Omega_1 \Omega_2 - \frac{1}{R_{CW}^2} \right) \left( \Omega_3 - \frac{1}{R_{LS}^2 \left( \Omega_2 - \frac{1}{R_{CW}^2 \Omega_1} \right)} \right) \quad (13)$$

so that $$V_3 = \frac{V_S}{\Omega_S} + \frac{V_M}{\Omega_M} \quad (14)$$

are the general transchest transfer function as shown in FIG. 4 or FIGS. 5a and 5b. Equation (14) incapsulates the transchest elements and their association between the forcing function $V_S$ (which models a defibrillation circuit and the shock pulse) and the cell membrane voltage $V_M$. Therefore, this completes the first step.

The variable $V_S$ may now be replaced with a more specific description of the defibrillation circuitry that implements a shock pulse. For a first example, a monophasic time-truncated, capacitive-discharge circuit may be represented by $V_S = V_1 e^{-t/\tau_1}$, where $V_1$ is the leading-edge voltage for the shock pulse and $\tau_1 = RC_1$, with R determined below.

As shown in FIGS. 5a and 5b, a second example would be a monophasic damped sine wave circuit, represented by $$V_S = V_1 \left( \frac{\tau_{C1}}{\tau_{C1} - \tau_{L1}} \right) (e^{-t/\tau_{C1}} - e^{-t/\tau_{L1}}) \quad (14B)$$

where $V_1$ is the voltage on the charged capacitor $C_1$, $\tau_{C1} = RC_1$ and $\tau_{L1} = L_1/R$. Every step illustrated below may be performed with this and other similar transchest forcing functions which represent defibrillator circuitry.

To proceed with step two, from FIG. 4, nodal analysis provides an equation for $V_M$:

$$C_M \frac{dV_M}{dt} + \frac{V_M - V_3}{R_M} = 0. \quad (15)$$

Rearranging equation 15, we have $$C_M \frac{dV_M}{dt} + \frac{V_M}{R_M} = \frac{V_3}{R_M}. \quad (16)$$

Next, substituting equation 14 as an expression for $V_3$ into equation 16, the cell membrane response is now calculated as follows:

$$C_M \frac{dV_M}{dt} + \frac{V_M}{R_M} = \frac{1}{R_M} \left( \frac{V_S}{\Omega_S} + \frac{V_M}{\Omega_M} \right) \quad (17)$$

$$C_M \frac{dV_M}{dt} + \frac{V_M}{R_M} - \frac{V_M}{R_M \Omega_M} = \frac{V_S}{R_M \Omega_S} \quad (18)$$

$$C_M \frac{dV_M}{dt} + \frac{V_M}{R_M} \left( 1 - \frac{1}{\Omega_M} \right) = \frac{V_S}{R_M \Omega_S}$$

Dividing through by $C_M$, and setting $\tau_M = R_M C_M$, then equation 18 becomes $$\frac{dV_M}{dt} + \frac{V_M}{\tau_M}\left(1 - \frac{1}{\Omega_M}\right) = \frac{V_S}{\tau_M}\left(\frac{1}{\Omega_S}\right). \quad (19)$$

Equation 19 is a general ordinary differential equation (ODE) that models the effects of any general forcing function $V_S$ that represents a phase of a shock pulse waveform applied across the chest. The general ODE equation 19 models the effects of a general shock pulse phase $V_S$ on the myocardium, determining cardiac cell response to such a shock pulse phase.

In the equations given below:

$C_1$ equals the capacitance of the first capacitor bank and $V_S = V_1 e^{-t/\tau_1}$;

$C_2$ equals the capacitance of the second capacitor bank and $V_S = V_2 e^{-t/\tau_2}$;

$R = R_S + R_B$, where $R_S$ = System impedance (device and electrodes);

$R_B$ = body impedance (thoracic cage, chest wall, lungs (series, parallel), heart).

To determine body impedance, $R_B$, we see that the series combination of $R_H$ and $R_{LS}$ yields $R_H + R_{LS}$. (FIG. 4). The parallel combination of $R_H + R_{LS}$ and $R_{LP}$ yields:

$$\frac{R_{LP}(R_{LS} + R_H)}{R_{LP} + R_{LS} + R_H}. \quad (20)$$

The series combination of equation 20 and $R_{CW}$ yields:

$$R_{CW} + \frac{R_{LP}(R_{LS} + R_H)}{(R_{LP} + R_{LS} + R_H)}. \quad (21)$$

The parallel combination of equation 21 and $R_{TC}$ yields:

$$R_B = \left[\frac{R_{TC}[R_{CW} + \frac{R_{LP}(R_{LS} + R_H)}{(R_{LP} + R_{LS} + R_H)}]}{R_{TC} + R_{CW} + \frac{R_{LP}(R_{LS} + R_H)}{(R_{LP} + R_{LS} + R_H)}}\right] \quad (22)$$

where $R_B$ is the impedance of the body for this model.

The discharge of a single capacitor is modeled by $V_S = V_1 e^{-t/\tau_1}$ for an initial $C_1$ capacitor voltage of $V_1$. Placing $V_S$ into equation 19 gives:

$$\frac{dV_M}{dt} + \frac{V_M}{\tau_M}\left(1 - \frac{1}{\Omega_M}\right) = \frac{V_1 e^{-t/\tau_1}}{\tau_M \Omega_S} \quad (23)$$

where $\tau_M = R_M C_M$ represents the time constant of the myocardial cell in the circuit model, and $\tau_1$, which equals $R_S C_1$, represents the time constant of $\phi_1$. Such a standard linear ODE as equation 23 has the form $$\frac{dy}{dx} + P(X)Y = Q(x).$$

These linear ODEs have an integration factor that equals $e^{\int P dx}$. The general solution to such equations is:

$$Y = e^{-\int P dx}[\int e^{\int P dx} Q dx + c].$$

The ODE in equation 23 models the effects of each phase of a time-truncated, capacitor-discharged shock pulse waveform. Equation 23 is a first-order linear ODE, and may be solved using the method of integration factors, to get:

$$V_{M1}(t) = k e^{-(t/\tau_M)\left(1 - \frac{1}{\Omega_M}\right)} + \left(\frac{V_1}{\Omega_S}\right)\left(\frac{\tau_1}{\tau_1\left(1 - \frac{1}{\Omega_M}\right) - \tau_M}\right) e^{-t/\tau_1}. \quad (24)$$

Equation 24 is an expression of cell membrane potential during $\phi_1$ of a shock pulse. To determine the constant of integration k, the initial value of $V_{M1}$ is assumed to be $V_{M1}(0) = V_G$ ("cell ground"). Applying this initial condition to equation 24, k is found to be $$k = V_G - \left(\frac{V_0}{\Omega_S}\right)\left(\frac{\tau_1}{\tau_1\left(1 - \frac{1}{\Omega_M}\right) - \tau_M}\right). \quad (25)$$

Assuming $\tau_1 = RC_1$, where $R = R_S + R_B$, then the solution to the initial-value problem for $\phi_1$ is:

$$V_{M1}(t) = V_G e^{-(t/\tau_M)\left(1 - \frac{1}{\Omega_M}\right)} + \quad (26)$$

$$\left(\frac{V_1}{\Omega_S}\right)\left(\frac{\tau_1}{\tau_1\left(1 - \frac{1}{\Omega_M}\right) - \tau_M}\right)\left(e^{-t/\tau_1} - e^{-(t/\tau_M)\left(1 - \frac{1}{\Omega_M}\right)}\right)$$

Equation 26 describes the residual voltage found on a cell at the end of $\phi_1$.

Assuming $V_G = 0$ and $V_1 = 1$, the solution for cell response to an external shock pulse is $$V_{M1}(t) = \left(\frac{1}{\Omega_S}\right)\left(\frac{\tau_1}{\tau_1\left(1 - \frac{1}{\Omega_M}\right) - \tau_M}\right)\left(e^{-\frac{t}{\tau_1}} - e^{-\left(\frac{t}{\tau_M}\right)\left(1 - \frac{1}{\Omega_M}\right)}\right). \quad (27)$$

We may now determine optimal durations for $\phi_1$ according to criteria for desired cell response. One such design role or criterion is that the $\phi_1$ duration is equal to the time required for the external defibrillator shock pulse to bring the cell response to its maximum possible level. To determine this duration, equation 27 is differentiated and the resulting equation 27B is set to zero. Equation 27B is then solved for the time t, which represents shock pulse duration required to maximize cardiac cell response.

$$\left(\frac{AB}{\tau_M}\right)e^{-Bt/\tau_M} - \left(\frac{A}{\tau_1}\right)e^{-t/\tau_1} = 0, \quad (27B)$$

where $$A = \left(\frac{1}{\Omega_S}\right)\left(\frac{\tau_1}{\tau_1\left(1 - \frac{1}{\Omega_M}\right) - \tau_M}\right)$$

and $$B = 1 - \frac{1}{\Omega_M}.$$

Solving for t, the optimal duration $d\phi_1$ for a monophasic shock pulse or $\phi_1$ of a biphasic shock pulse is found to be $$d\phi_1 = \left( \frac{\tau_1 \tau_M}{\tau_1\left(1 - \frac{1}{\Omega_M}\right) - \tau_M} \right) \ln\left( \frac{\tau_1\left(1 - \frac{1}{\Omega_M}\right)}{\tau_M} \right), \quad (27C)$$

where "ln" represents the logarithm to the base e, the natural logarithm.

For $\phi_2$, an analysis almost identical to equations 20 through 27 above is derived. The differences are two-fold. First, a biphasic waveform reverses the flow of current through the myocardium during $\phi_2$. Reversing the flow of current in the circuit model changes the sign on the current. The sign changes on the right hand side of equation 23.

The second difference is the step taken to incorporate an independent $\phi_2$ into the charge burping model. Therefore, the $\phi_2$ ODE incorporates the $C_2$ capacitor set and their associated leading-edge voltage, $V_2$, for the $\phi_2$ portion of the pulse. Then $\tau_2$ represents the $\phi_2$ time constant; $\tau_2 = RC_2$, and $V_S = -V_2 e^{-t/\tau_2}$. Equation 23 now becomes:

$$\frac{dV_M}{dt} + \left(\frac{V_M}{\tau_M}\right)\left(1 - \frac{1}{\Omega_M}\right) = \frac{-V_2 e^{-t/\tau_2}}{\tau_M \Omega_S}. \quad (29)$$

Equation 29 is again a first-order linear ODE. In a similar manner, its general solution is determined to be:

$$V_{M2}(t) = k e^{(-t/\tau_M)\left(1 - \frac{1}{\Omega_M}\right)} - \left(\frac{V_2}{\Omega_S}\right)\left( \frac{\tau_2}{\tau_2\left(1 - \frac{1}{\Omega_M}\right) - \tau_M} \right). \quad (30)$$

To determine the constant of integration k, the value of $V_{M2}$ at the end of $\phi_1$ is $$V_{M2}(0) = V_{M1}(d_{\phi 1}) = V_{\phi 1}, \quad (31)$$

where $d_{\phi 1}$ is the overall time of discharge for $\phi_1$ and $V_{\phi 1}$ is the voltage left on the cell at the end of $\phi_1$. Applying the initial condition to equation 30 and solving for k:

$$k = V_{\phi 1} + \left(\frac{V_2}{\Omega_S}\right)\left( \frac{\tau_2}{\tau_2\left(1 - \frac{1}{\Omega_M}\right) - \tau_M} \right). \quad (32)$$

The solution to the initial-value problem for $\phi_2$ is $$V_{M2}(t) = \left(\frac{V_2}{\Omega_S}\right)\left( \frac{\tau_2}{\tau_2\left(1 - \frac{1}{\Omega_M}\right) - \tau_M} \right)\left( e^{-(t/\tau_M)\left(1 - \frac{1}{\Omega_M}\right)} - e^{-t/\tau_2} \right) + V_{\phi 1} e^{-(t/\tau_M)\left(1 - \frac{1}{\Omega_M}\right)}. \quad (33)$$

Equation 33 provides a means to calculate the residual membrane potential at the end of $\phi_2$ for the cells that were not stimulated by $\phi_1$. Setting Equation 33 equal to zero, we solve for t, there by determining the duration of $\phi_2$, denoted $d\phi_2$, such that $V_{M2}(d\phi_2) = 0$. By designing $\phi_2$ with a duration $d\phi_2$, the biphasic shock pulse removes the residual change placed on a cell by $\phi_1$. We determine $d\phi_2$ to be:

$$d\phi_2 = \left( \frac{\tau_2 \tau_M}{\tau_2\left(1 - \frac{1}{\Omega_M}\right) - \tau_M} \right) \cdot \ln\left( 1 + \left( \frac{\tau_2\left(1 - \frac{1}{\Omega_M}\right) - \tau_M}{\tau_2} \right)\left( \frac{\Omega_S V_{\phi 1}}{V_2} \right) \right). \quad (34)$$

From the equations above an optimal monophasic or biphasic defibrillation waveform may be calculated for an external defibrillator.

As an example, an external defibrillator may be designed as set forth below. Assume a monophasic truncated exponential shock pulse, a 200 μF capacitor, so that $\tau_1 = R \cdot (200 \mu F)$. Suppose also that the external defibrillator is designed to apply the maximal cardiac cell response design rule (equation 27C) to determine the duration of the discharge. Suppose further that the human cardiac cell time constant is estimated to be 3±1 ms. Further assume that the external defibrillator energy source comprises five 1000 μF capacitors in series to implement a 200 μF capacitor bank. If each capacitor is charged to 400V, for a total of 2000V for the leading-edge voltage this represents 400 J of stored energy. The transchest elements are estimated at: 82% current through the thoracic cage; 14% through the chest wall and lungs in parallel; and 4% of applied current through the lung in series with the heart. Then the membrane resistance coefficient $\Omega_M = 5.9$, and the system resistance coefficient $\Omega_S = 2.3$. Then the table below illustrates the application of the design rule as the overall chest resistance ranges from 25Ω to 200Ω:

| R (Ω) | $\tau_1$ | d($\phi$1) (ms) | $V_{final}$ (V) | $E_{delivered}$ (J) |
| --- | --- | --- | --- | --- |
| 25  | 5.2  | 5.05  | 757  | 343 |
| 50  | 10.2 | 6.90  | 1017 | 297 |
| 75  | 15.2 | 8.15  | 1170 | 263 |
| 100 | 20.2 | 9.10  | 1275 | 238 |
| 125 | 25.2 | 9.90  | 1350 | 216 |
| 150 | 30.2 | 10.55 | 1410 | 201 |
| 175 | 35.2 | 11.15 | 1457 | 186 |
| 200 | 40.2 | 11.65 | 1497 | 176 |

Description of a Single Capacitor/Inductor Circuit

Having developed the transthoracic model above, a general description of a single capacitor/inductor circuit will now be given.

Figure 6:
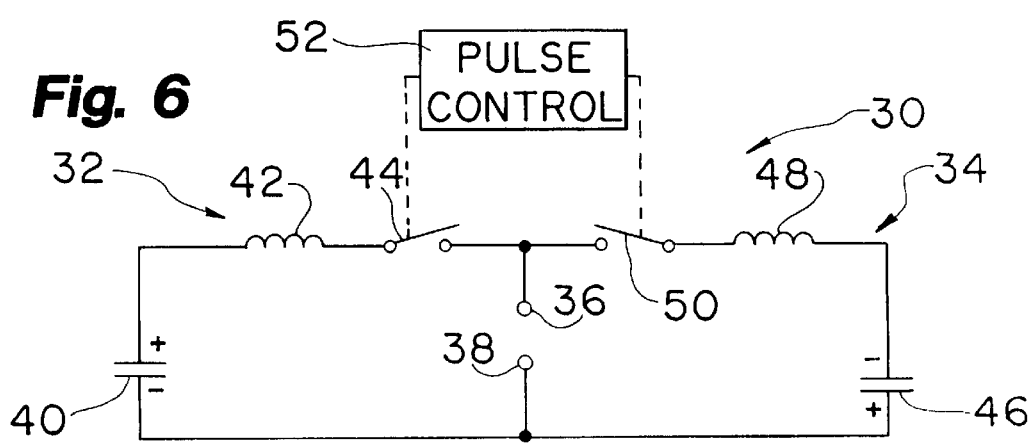
FIG. 6 is a simplified schematic illustration of an external defibrillation sinusoidal pulse generating circuit.

FIG. 6 is a simplified schematic illustration of a general external defibrillation pulse generation circuit 30 which is configured for producing truncated damped sinusoidal biphasic (i.e., multiphasic) and/or monophasic defibrillation pulses (without the external modeling parameters of FIGS. 4 and 5). As shown, circuit 30 includes a first pulse component generation circuit 32 and a second pulse component generation circuit 34 which are connected in a parallel arrangement to a pair of electrode terminals 36 and 38. First pulse component generation circuit 32 includes a charge storage device such as capacitor 40, an inductor 42 and a circuit or device represented by switch 44 connected to one another in a series arrangement between terminals 36 and 38. Similarly, second pulse component generation circuit 34 includes a capacitor 46, an inductor 48 and a switch 50 connected to one another in a series arrangement between terminals 36 and 38. Switches 44 and 50 are coupled to and are independently controlled by a pulse controller 52 to initiate and terminate (truncate) defibrillation pulses.

Figure 2A:
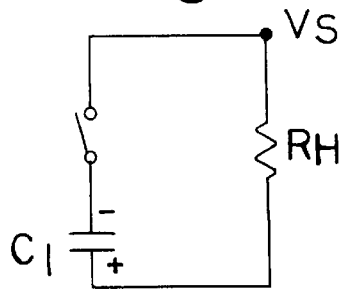
FIG. 2a is a very simplified defibrillator model.
Figure 2B:
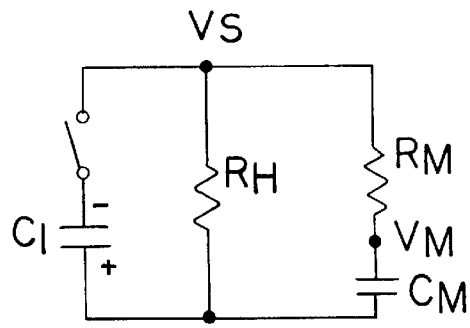
FIG. 2b is a known monophasic defibrillation model.
Figure 3:
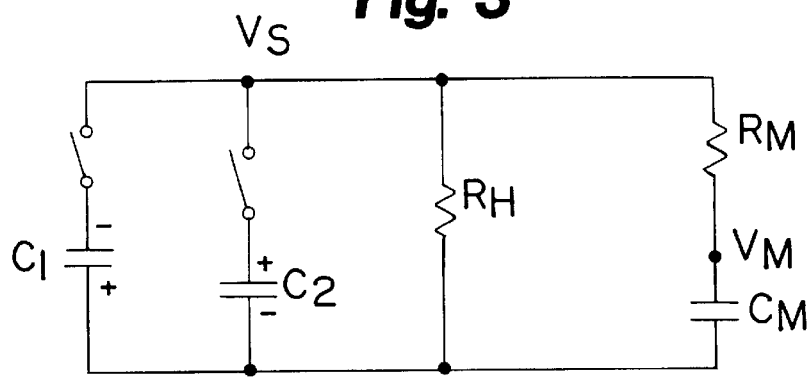
FIG. 3 is a known biphasic defibrillation model.

The defibrillation pulses generated by circuit 30 will be applied to the torso of a patient in a conventional manner through a pair of electrodes, such as electrodes 24 from FIG. 2, electrically connected to terminals 36 and 38. In one embodiment capacitors 40 and 46 are in the range of 25 µF–500 µF, and inductors 42 and 48 are in the range of 25 mH–500 mH. Estimated optimal values for capacitors 40 and 46 and inductors 42 and 48 are chosen for AED 10. In one embodiment, capacitor 40 is chosen to be 45 µF, capacitor 46 is chosen to be 180 µF, inductor 42 is chosen to be 250 mH and inductor 48 is chosen to be 250 mH.

Figure 7:
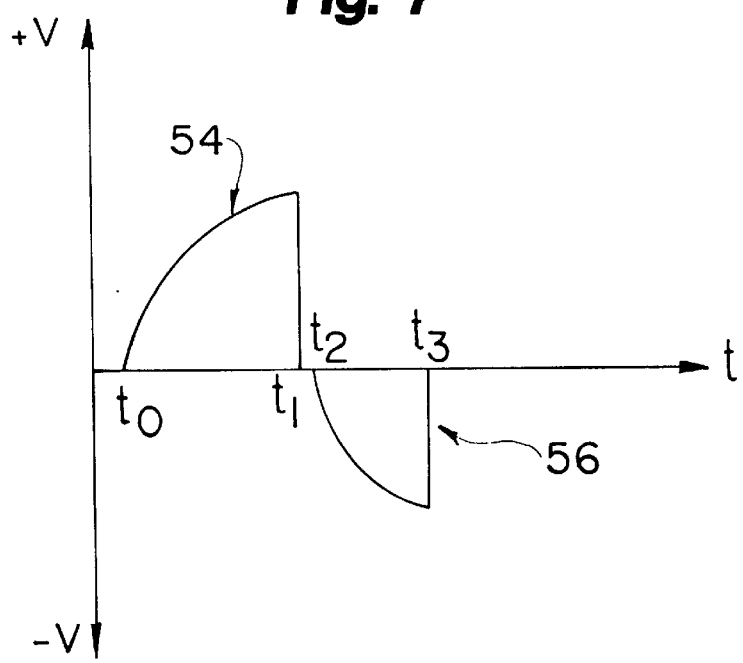
FIG. 7 is an illustration of a single capacitor truncated damped sinusoidal biphasic defibrillation pulse.

FIG. 7 is an illustration of a single capacitor truncated damped sinusoidal biphasic defibrillation pulse which includes a first phase having a positive polarity component 54 and a second phase having a negative polarity pulse component 56. With capacitors 40 and 46 charged to their respective opposite polarity charge potentials, pulse controller 52 causes the circuit element(s) forming switch 44 to switch to a closed state at time $t_0$ to initiate first phase pulse component 54. At time $t_1$ switch 44 is switched to an open state to terminate pulse component 54. Although not shown in FIG. 7, pulse component 54 can also be truncated by circuitry controlled by pulse controller 52 which rapidly discharges capacitor 40 and inductor 42. Second phase pulse component 56 is initiated by pulse controller 52 at time $t_2$ by switching switch 50 to a closed state. At time $t_3$ switch 50 is switched to an open state to truncate second phase pulse component 56.

Figure 8A:
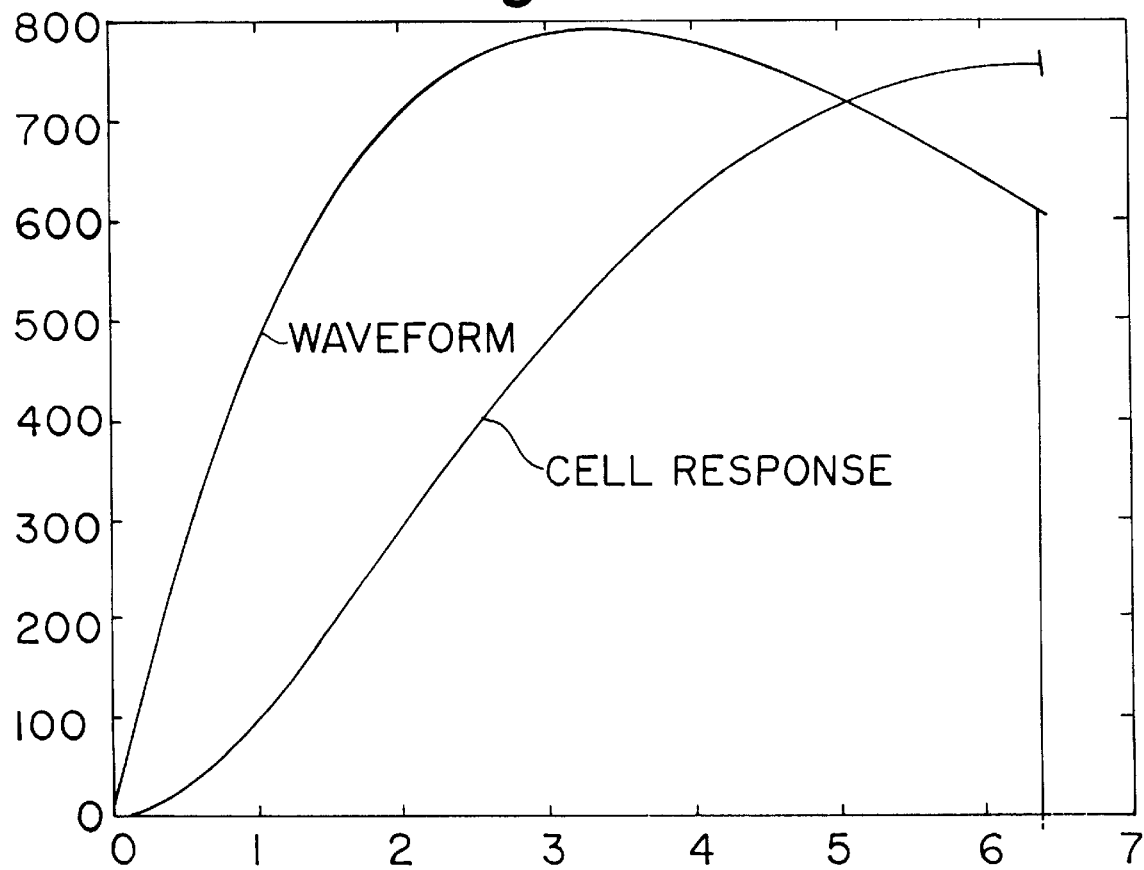

It has been determined that one preferred and efficacious waveform has first phase component 54 with a relatively slow onset with respect to a convention damped sinusoidal pulse. In particular, the shape of first phase pulse component 54 can be tailored in an attempt to match the cell membrane response to the first pulse component. These preferred characteristics of first phase component 54 are illustrated generally in FIGS. 8a, 8b and 8c. FIG. 8a illustrates a damped sinusoidal pulse waveform and the associated cell membrane response. This diagram assumes an 80Ω load for the heart, capacitor 40 is 45 µF and inductor 42 is 250 mH.

Figure 8B:
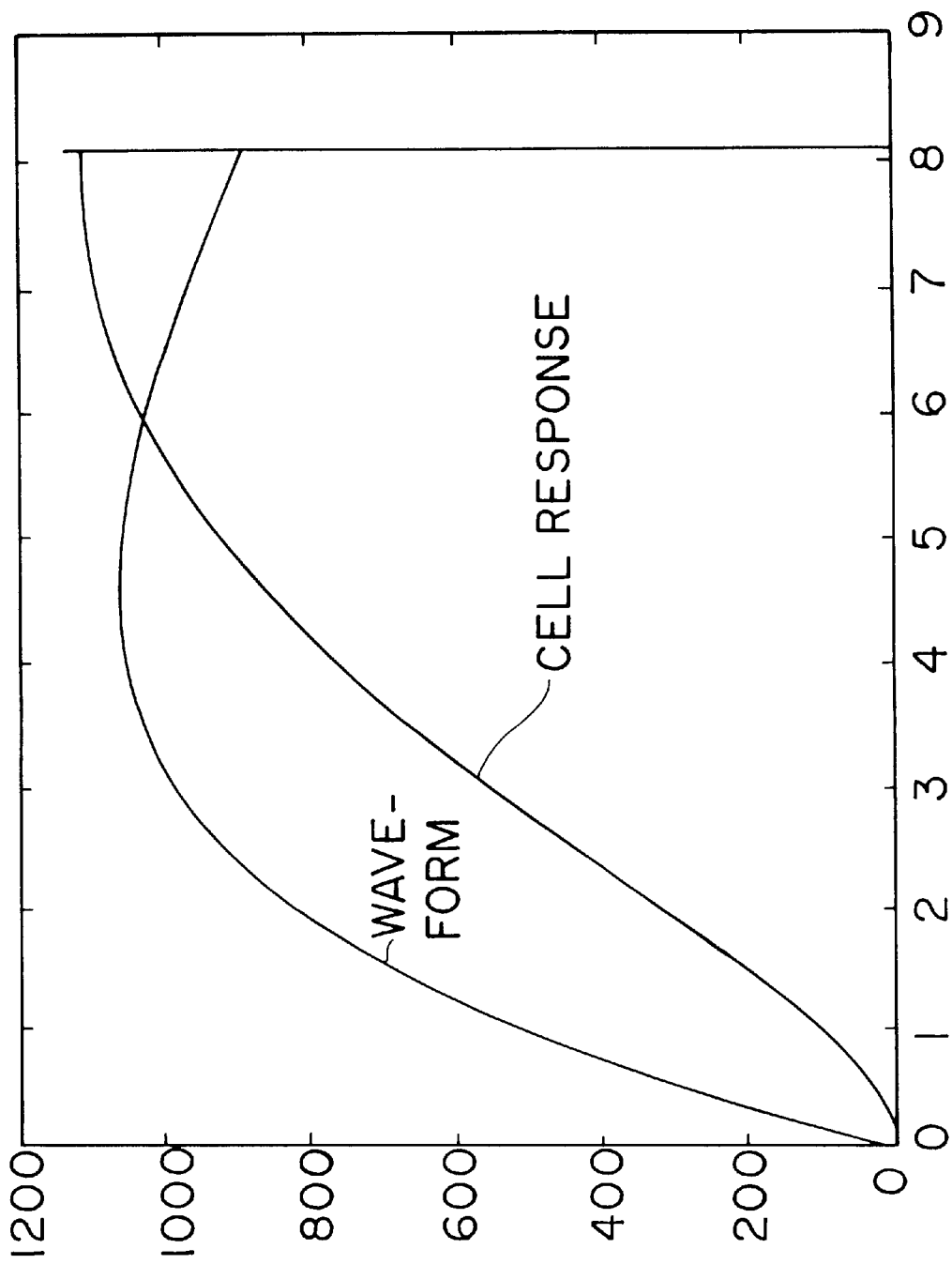

The damped sinusoidal pulse waveform shown in FIG. 8b has a slower onset than that of the waveform shown in FIG. 8a, with little or no loss in the onset time of the associated cell membrane response. In this embodiment, an 80Ω load is again assumed for the heart, capacitor 40 is 90 µF and inductor 42 is 250 mH. The damped sinusoidal pulse waveform shown in FIG. 8c has an even slower onset time than that of the waveform shown in FIG. 8b, and again generates an associated cell membrane response with little or no loss in the onset time with respect to the cell membrane response generated by the waveform shown in FIG. 8a. In this embodiment, an 80Ω load is again assumed, capacitor 40 is 180 µF and inductor 42 is again 250 mH.

Another preferred and effacious waveform has first phase component 54 which is truncated at a time which closely corresponds to the time that the maximum or peak cell membrane response is achieved (i.e., when the slope of the cell membrane response is zero). First phase components 54 having these characteristics are also illustrated in FIGS. 8a, 8b and 8c. Defibrillation efficacy can thereby be maximized with respect to the peak cell response design rule using relatively low energy and short waveforms.

The ability of circuit 30 to independently generate and shape second phase pulse component 56 also contributes to the efficacy of the waveform. In particular, this characteristic of the circuit enables second phase pulse component 56 to be tailored in voltage, length, shape and other characteristics to maximize its charge burping effects on the cell membrane. For example, second phase component 56 can have a duration which is different than the duration of first phase component 54, and which is truncated at the time that the cell membrane response reaches about zero.

In operation a single capacitor/inductor truncated damped sine wave is developed and applied to a patient that approximates the patient's cell response and that truncates at the peak cell response. In order to develop a waveform that matches (or attempts to match) the cell response, it is first necessary to measure a patient dependent parameter, such as impedance, voltage, current, charge or other measurable parameters of the patient. The values of capacitors 40 and 46, and inductors 42 and 48 are preselected, thus once the patient dependent parameter is determined a first duration of a monophasic or $\phi_1$, of a biphasic waveform can be determined using the equations developed above for modeling a human chest. In particular, solving for t in equation 36 below yields the optimal duration $d\phi$ for a monophasic or $\phi_1$ of a biphasic waveform. Equation 39 below is used to determine the optimal duration for $\phi_2$ of the biphasic waveform. As can be appreciated from the above, the determination of the optimal duration of $\phi_2$ is independent from that of $\phi_1$.

After the optimal durations have been determined, capacitor 40 is charged. For biphasic waveforms, capacitor 42 is also charged. Switch 44 is then closed discharging capacitor 40 to electrical terminals 36 and 38. At the end of the optimally calculated duration $d\phi_1$, switch 44 is opened to truncate the phase one waveform. Switch 50 is then closed discharging capacitor 42 to electrode terminals 36 and 38. At the end of the optimally calculated duration $d\phi_2$ switch 50 is opened to truncate the $\phi_2$ portion of the biphasic waveform.

The design rules for the truncated damped sine waveform are now developed. Equation 19 is now used to solve for $V_M$ by replacing $V_S$ with the defibrillation circuit model for a damped sine waveform, as shown in equation 14B. Doing so provides:

$$\frac{dV_M}{dt} + \frac{V_M}{\tau_M}\left(1 - \frac{1}{\Omega_M}\right) = \left(\frac{V_1}{\tau_M \Omega_S}\right)\left(\frac{\tau_{CI}}{\tau_{CI} - \tau_{LI}}\right)\left(e^{\frac{-t}{\tau_{CI}}} - e^{\frac{-t}{\tau_{LI}}}\right). \quad (35)$$

The solution of equation 35 for $V_M$ is found in the same manner as described above for equations 24–27, so that $$V_{MI}(t) = L_{11} \cdot \left(e^{-\left(\frac{t}{\tau_{CI}}\right)} - e^{-\left(\frac{t}{\tau_M}\right)\left(1 - \frac{1}{\Omega_M}\right)}\right) - \quad (36)$$
$$L_{12} \cdot \left(e^{-\left(\frac{t}{\tau_{LI}}\right)} - e^{-\left(\frac{t}{\tau_M}\right)\left(1 - \frac{1}{\Omega_M}\right)}\right)$$

where $$L_{11} = \left(\frac{V_1}{\Omega_S}\right)\left(\frac{\tau_{CI}}{\tau_{CI} - \tau_{LI}}\right)\left(\frac{\tau_{CI}}{\tau_{CI}\left(1 - \frac{1}{\Omega_M}\right) - \tau_M}\right) \quad (37)$$

and $$L_{12} = \left(\frac{V_1}{\Omega_S}\right)\left(\frac{\tau_{CI}}{\tau_{CI} - \tau_{LI}}\right)\left(\frac{\tau_{LI}}{\tau_{LI}\left(1 - \frac{1}{\Omega_M}\right) - \tau_M}\right) \quad (38)$$

To maximize cell response, $V_{M1}(t)$ is differentiated, the derivative $(dV_{M1}(t)/dt)$ is to zero, and the time t is determined such that $(dV_{M1}(t)/dt)=0$. The time t solution of the differential equation of $V_{M1}(t)$ provides the design rule for the duration of $\phi_1$ of the truncated damped sine waveform.

Figure 9:
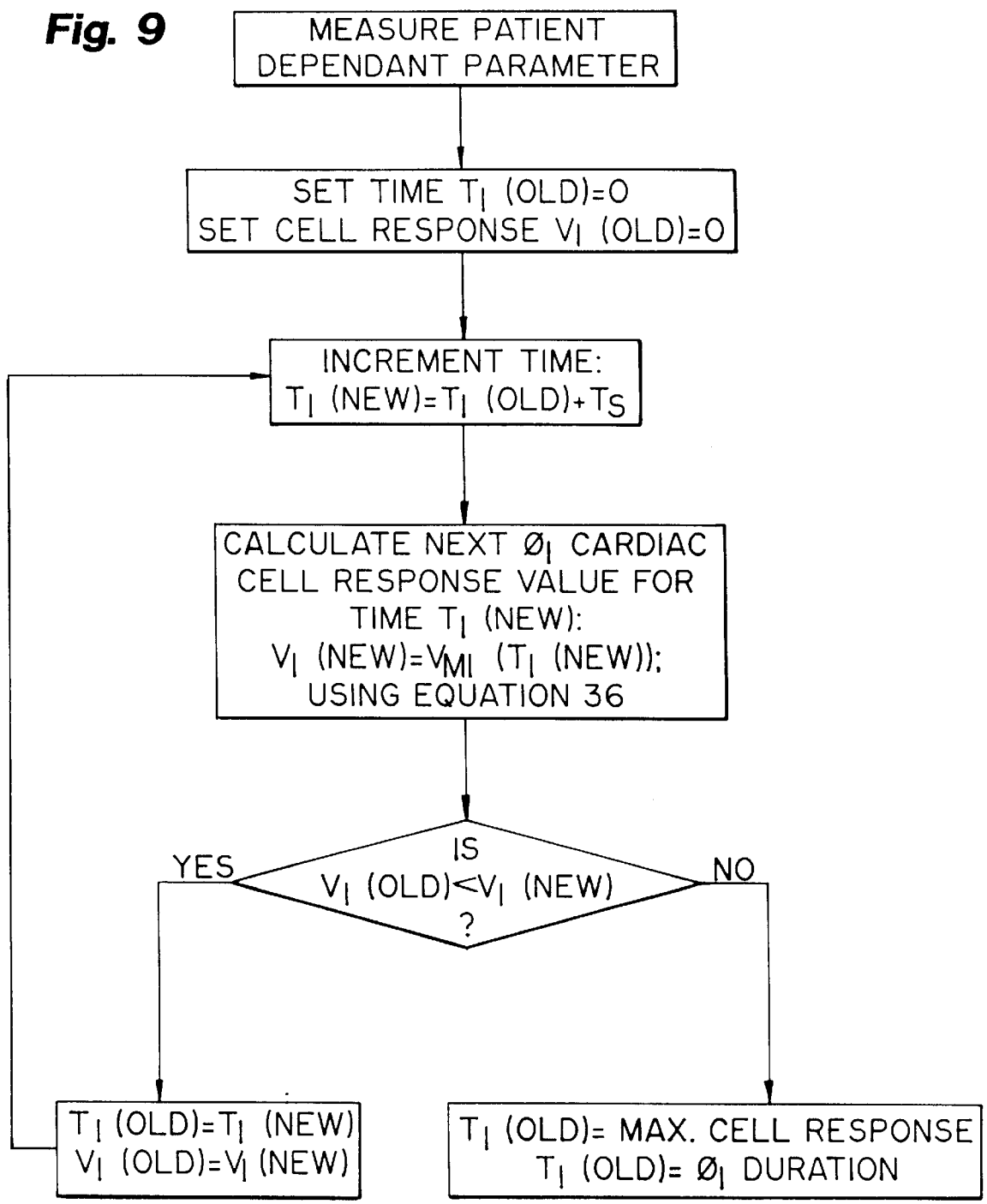
FIG. 9 illustrates a flow chart for the determination and use of the truncation time for $\phi_1$ of a damped sine wave shock pulse.

For a predetermined time step $T_S$ (for example 50 ms) a real-time implementation of the truncation process is described in FIG. 9 for $\phi_1$ of the damped sine wave shock pulse. The time $T_1$(old) determined from this process is the time of maximum cell response and therefore the duration of $\phi_1$.

In the same manner that equation 33 is derived, the cardiac cell response to $\phi_2$ of a damped sine wave shock pulse is found to be $$V_{M2}(t) = L_{21}\left(e^{-\left(\frac{t}{\tau_{L2}}\right)} - e^{-\left(\frac{t}{\tau_M}\right)\left(1-\frac{1}{\Omega_M}\right)}\right) - \tag{39}$$
$$L_{22}\left(e^{\left(\frac{-t}{\tau_{C2}}\right)} - e^{-\left(\frac{t}{\tau_M}\right)\left(1-\frac{1}{\Omega_M}\right)}\right) + \left[V_{\phi 1}e^{-\left(\frac{t}{\tau_M}\right)\left(1-\frac{1}{\Omega_M}\right)}\right]$$

in accordance with FIG. 5b; where $$L_{21} = \left(\frac{V_2}{\Omega_S}\right)\left(\frac{\tau_{C2}}{\tau_{C2}-\tau_{L2}}\right)\left(\frac{\tau_{L2}}{\tau_{L2}\left(1-\frac{1}{\Omega_M}\right)-\tau_M}\right) \tag{40}$$

and $$L_{22} = \left(\frac{V_2}{\Omega_2}\right)\left(\frac{\tau_{C2}}{\tau_{C2}-\tau_{L2}}\right)\left(\frac{\tau_{C2}}{\tau_{C2}\left(1-\frac{1}{\Omega_M}\right)-\tau_M}\right) \tag{41}$$

and $$V\phi_1 = V_{M1}(d_1)$$

and
where $d_1$ is the duration for $\phi_1$ of the damped sine wave shock pulse. To determine the $\phi_2$ design rule, equation 39 is set to zero and the time t is determined such that $V_{M2}(t)=0$. A real-time implementation of $\phi_2$ truncation process is described in FIG. 10.

Description of Stepped-Capacitor/Inductor Damped Sine Wave Model

Embodiments of the invention provide a method and apparatus for delivering a stepped truncated damped sinusoidal waveform that defibrillates the heart based on models of the cell response. These embodiments truncate the monophasic pulse or $\phi_1$ of a biphasic pulse at the peak or approximate peak cell response time. These embodiments truncate the $\phi_2$ of a biphasic pulse at the time the cell response has indicated that the cell is reset to a natural resting potential. Additionally, these embodiments provide a waveform that attempts to approximate a constant current waveform.

Figure 11:
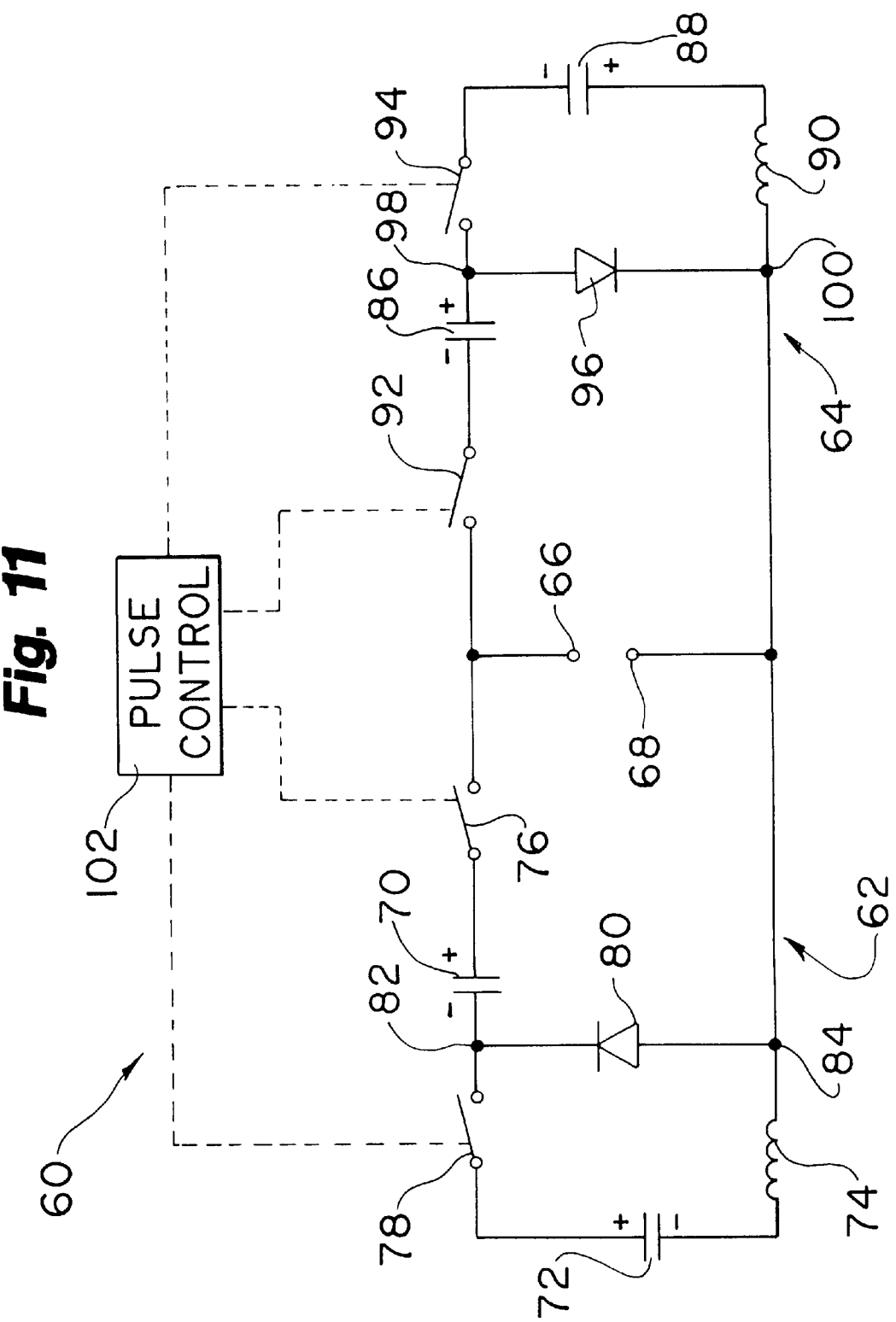
FIG. 11 is a simplified stepped capacitor truncated damped sinusoidal biphasic circuit according to the invention.

FIG. 11 is a schematic illustration of an external defibrillation pulse generation circuit 60 which is configured for producing stepped truncated damped sinusoidal biphasic (i.e. multiphasic) and/or monophasic defibrillation pulses according to embodiments of the invention. As shown, circuit 60 includes a first pulse component generation circuit 62 and a second pulse component generation circuit 64 which are connected in a parallel arrangement to a pair of electrode terminals 66 and 68. First pulse component generation circuit 62 includes first and second charge storage devices such as capacitors 70 and 72, inductor 74 and first and second circuits or other devices represented by switches 76 and 78 connected to one another in a series arrangement between terminals 66 and 68. A diode 80 is connected at node 82 which is between capacitor 70 and switch 78 and 84 which is between inductor 74 and electrode 68. Similarly, second pulse component generation circuit 64 includes first and second capacitors 86 and 88, inductor 90 and first and second switches 92 and 94, connected to one another in a series arrangement between terminals 66 and 68. A diode 96 is connected at node 98 which is between capacitor 86 and switch 94 and node 100 which is between conductor 90 and electrode 68. Switches 76, 78, 92 and 94 are coupled to and independently controlled by a pulse control circuit 102 to initiate and truncate (terminate) defibrillation pulses. The defibrillation pulses generated by circuit 60 will be applied to the torso of a patient in a conventional manner through a pair of electrodes (as illustrated in FIG. 1) electrically connected to terminal 66 and 68.

Figure 12:
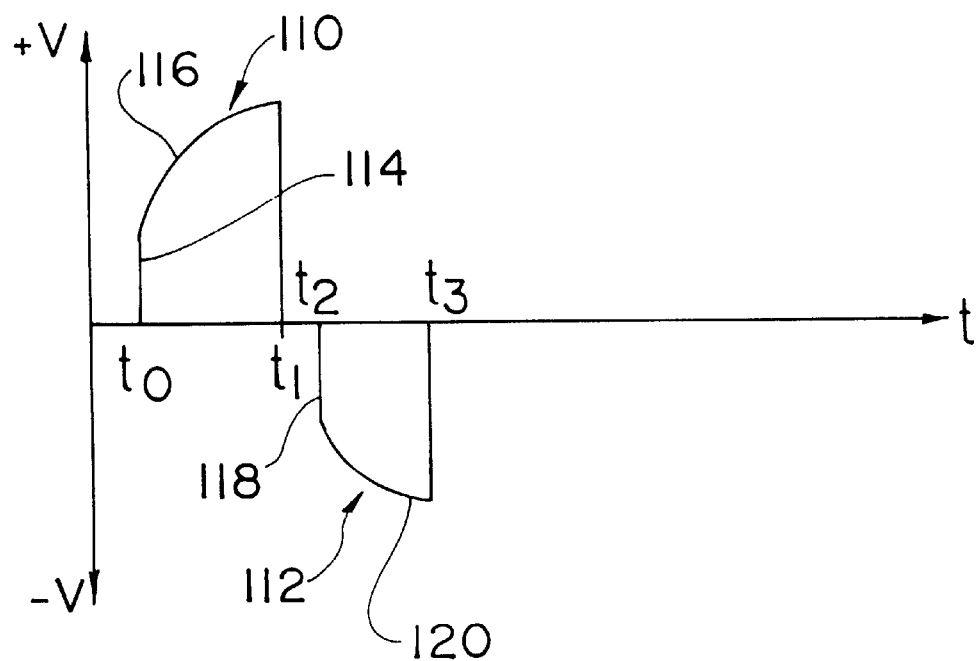
FIG. 12 is an illustration of a stepped truncated damped sine wave produced by a circuit as in FIG. 11, in which the times between closing switches 76 and 78 or between closing switches 92 and 94 are short.

FIG. 12 is an illustration of a stepped truncated damped sinusoidal biphasic defibrillation pulse which includes a first phase and positive polarity component 110 and a second phase and negative polarity pulse component 112. To generate the pulse shown in FIG. 12, capacitors 70 and 72 are charged to their desired first polarity charge potentials, while capacitors 86 and 88 are charged to their desired and opposite second polarity charge potentials. At time $t_0$ pulse control circuit 102 causes the circuit elements forming switch 76 to switch to a closed state to initiate first phase pulse component 110 with voltage step 114. Very quickly (e.g. less than about 1 ms, and before capacitor 70 discharges to any substantial degree) after switch 76 has been closed, pulse control circuit 102 switches switch 78 to a closed state to initiate the sinusoidal component 116 of first phase pulse component 110. At time $t_1$ switches 76 and 78 are switched to an open state to terminate pulse component 110. Although not shown in FIG. 11, first phase pulse component 110 can also be truncated by circuitry controlled by pulse control circuit 102 which rapidly discharges capacitors 70 and 72 and inductor 74. A voltage step 118 of second phase pulse component 112 is initiated by pulse control circuit 102 at time $t_2$ by switching switch 92 to a closed state. Very quickly thereafter (i.e., before capacitor 86 substantially discharges), switch 94 is closed by pulse control circuit 102 to initiate the sinusoidal component 120 of pulse component 112. At time $t_3$ switches 92 and 94 are switched to an open state to truncate second phase pulse component 112. Defibrillation pulse components 110 and 112 provide an initial step of voltage and current to rapidly initiate the cell membrane response, and are efficacious.

Figure 13:
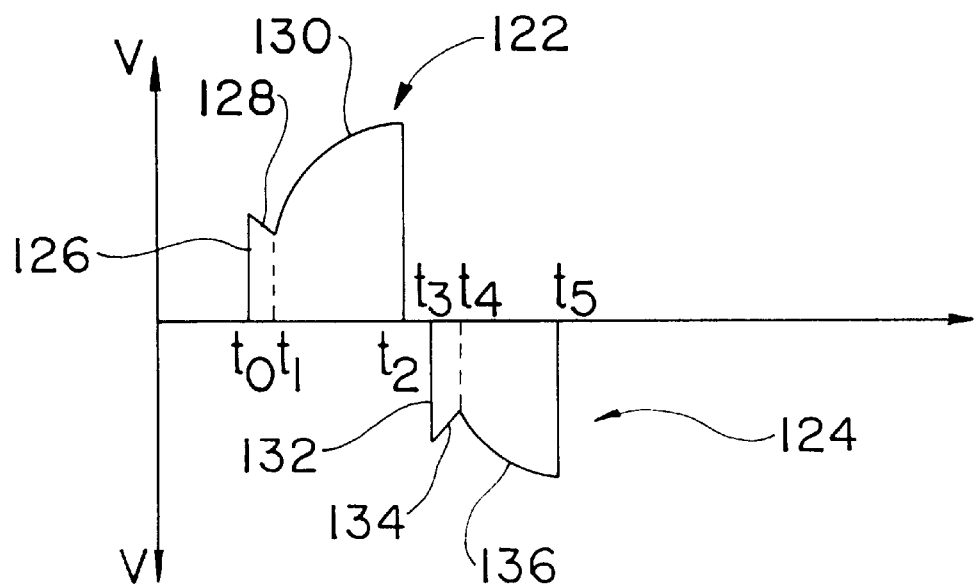
FIG. 13 is an illustration of a stepped truncated damped sine wave produced by a circuit as in FIG. 11, in which the times between closing switches 76 and 78 or between closing switches 92 and 94 are long.

FIG. 13 is an illustration of a two-part stepped truncated damped sinusoidal biphasic defibrillation pulse according to embodiments of the invention which can be generated by circuit 60 shown in FIG. 11. As shown, the pulse includes a first phase and positive polarity component 122 and a second phase and negative polarity pulse component 124. To generate the pulse capacitors 70 and 72 are charged to their desired first polarity charge potentials, while capacitors 86 and 88 are charged to their desired and opposite second polarity charge potentials. At time $t_0$ pulse control circuit 102 causes the circuit elements forming switch 76 to switch to a closed state to initiate first phase pulse component 122 with voltage step 126. The maximum voltage of step 126 will be the charge potential on capacitor 70. Between time $t_0$ and time $t_1$ switch 76 remains in its closed state and switch 78 in its open state to provide an exponential decay component 128. At time $t_1$ pulse control circuit 102 switches switch 78 to a closes state to initiate a sinusoidal component 130 of first phase pulse component 122. A time $t_2$ switches 76 and 78 are switched to an open state to terminate pulse component 122. Although not shown in FIG. 11, first phase pulse component 122 can also be truncated by circuitry controlled by pulse control circuit 102 which rapidly discharges capacitors 70 and 72 and inductor 74. Voltage step 132 of second phase pulse component 124 is initiated by pulse control circuit 102 at time $t_3$ by switching switch 92 to a closed state. The maximum voltage of step 132 will be the charge potential on capacitor 86. Between time $t_3$ and $t_4$ switch 92 remains in its closed state and switch 94 in its open state to provide an exponential decay component 134. At time $t_4$ pulse control circuit 102 switches switch 94 to a closed state to initiate a sinusoidal component 136 of pulse component 124. At time $t_5$ switches 92 and 94 are switched to an open state to truncate second phase pulse component 124. Defibrillation pulses of the type shown in FIG. 13 provide an initial step of voltage and current, as well as a short expotential decay, to rapidly initiate cell membrane response, and are efficacious.

Optimal characteristics for defibrillation pulse waveforms and the component values of circuit 60 for generating the waveforms can be determined using the design methodology described above.

Embodiments of the invention provide for a higher effective current than does the single capacitor/inductor circuit of FIG. 6. By providing a rapid boost in the delivery of the waveform, the peak cell response is obtained quicker which produces a more efficient waveform. Additionally, embodiments of the invention allow for reducing the size of the inductor while still providing an effective and efficient waveform which saves cost, size and weight. Embodiments of the invention also more closely approximate a constant current waveform, which have been proven to be the most efficacious.

The design rules and methodology for the stepped capacitor damped sine waveform are described below. Equation 19 is used to solve for $V_M$ by replacing $V_S$ with the defibrillation circuit model for a stepped capacitor damped sine waveform, as shown in the first pulse component generation circuit 62 of FIG. 11. The stepped capacitor damped sine wave model is described by:

$$L_2 \frac{di}{dt} + \frac{1}{C_2}\int i\, dt + \frac{1}{C_1}\int i\, dt + R_H i = 0, \quad (42)$$

where $C_1$ represents capacitor 70, $C_2$ represents capacitor 72 and $L_2$ represents inductor 74.

As stated above, the circuit in FIG. 11 operates as set forth below; capacitors 70 and 72 are charged. Switch 76 is then closed for a period of time. At the end of that time period, switch 78 is closed. Therefore, voltage at the time $d_1$ switch 76 is closed is equal to $$V_S(d_1) = V_1 e^{\frac{-d_1}{\tau_1}},$$

where $\tau_1 = R C_1$. So, at the time that switch 78 is closed, equation 42 is rewritten as $$\frac{di}{dt} + \frac{i}{\tau_L} = \frac{i_C}{\tau_L} \quad (43)$$

where $$\tau_L = \frac{L_2}{R_H} \text{ and } i_c = \frac{V_0}{R_H} e^{-t/\tau_C},$$

Also:

$$\tau_c = R \cdot C_0;\ C_0 = \frac{C_1 \cdot C_2}{C_1 + C_2} \text{ and } V_0 = V_1 + V_2,$$

where $V_1$ is the voltage on $C_1$ and $V_2$ is the voltage on $C_2$.

The solution to equation 43 and thereby the description for the stepped capacitor damped sine wave model is $$V_S(t) = \left[V_S(d_1) - \left(\frac{V_0 \tau_C}{\tau_C - \tau_L}\right)\right] e^{-t/\tau_L} + \left(\frac{V_0 \tau_C}{\tau_C - \tau_L}\right) e^{-t/\tau_C} \quad (44)$$

The stepped capacitor damped sine wave model operates as a single capacitor discharge for a time from 0 to $d_1$ in duration. This is the time that switch 76 is closed and switch 78 is open. The cell response during this time is described by equation 27, so that at the moment immediately prior to closing switch 78, the cell response is $V_{M1}(0) = V_{M11}(d_1)$, where $V_{M11}$ designates the cell response to the stepped capacitor damped sine wave after closing switch 76 and prior to closing switch 78, and $V_{M12}$ designates the cell response following the closing of switch 78, all during $\phi_1$ of the waveform (or the only phase, if the waveform is monophasic). Therefore, in general, the $\phi_1$ cell response to the model at time $t \geq d_1$ is:

$$V_{M1}(t) = V_{M11}(d_1) e^{-t/\tau_M} + V_{M12}(t).$$

The description of the cell response $V_{M12}(t)$ is $$V_{M12}(t) = L_{11}\left(e^{-t/\tau_L} - e^{-(t/\tau_M)\left(1 - \frac{1}{\Omega_M}\right)}\right) + \quad (45)$$

$$L_{12}\left(e^{-t/\tau_C} - e^{-(t/\tau_M)\left(1 - \frac{1}{\Omega_M}\right)}\right),$$

with $$L_{11} = \left[\frac{V(d_1) - V_0\left(\frac{\tau_C}{\tau_C - \tau_L}\right)}{\Omega_S}\right]\left(\frac{\tau_L}{\tau_L\left(1 - \frac{1}{\Omega_M}\right) - \tau_M}\right) \quad (46)$$

and $$L_{12} = \left[\left(\frac{V_0}{\Omega_S}\right)\left(\frac{\tau_C}{\tau_C - \tau_L}\right)\right]\left(\frac{\tau_C}{\tau_C\left(1 - \frac{1}{\Omega_M}\right) - \tau_M}\right). \quad (47)$$

The design rule for the stepped capacitor damped sine wave is to deliver the waveform shock pulse for a time $d_2 > d_1$ such that the cell response is maximized. This defines the optimal duration for the first phase $\phi_1$ of the shock pulse. This also defines the optimal duration for a monophasic shock pulse. FIG. 9 describes the determination of $d_2$ and thereby implementation of the monophasic shock pulse or $\phi_1$ of a biphasic shock pulse, so that $V_{M1}(d_2)$ is the desired cell response.

In one preferred embodiment, the duration $d_1$ is predetermined and short by comparison to the total length $d_2$. This $d_1$ provides the jump start to $V_1$ that the shock pulse requires in order to simulate a square wave, or constant current, shock pulse. An illustrative example will now be given. It should be noted that the values chosen are simply examples and are not meant to limit the invention in any way. The duration $d_1$ is chosen to be less than 1 ms, and in particular, 0.1 ms. This means that switch 76 is closed and switch 78 is open for this period of time. At time $d_1$ switch 78 is closed until time $d_2$. Time $d_2$ is predetermined as described in FIG. 9. The shock pulse and associated cell response are shown as $\phi_1$ of the waveform in FIG. 14. Equation 27 describes the cell response due to closing switch 76 prior to closing switch 78. This cell response is expressed by $V_{M11}(d_1)$ and represents a portion of the total cell response. Therefore, $V_{M1}$, over the time 0 to time $(d_1+d_2)$, expresses the cumulative cell response to a stage or pulse component generation circuit.

Figure 15A:
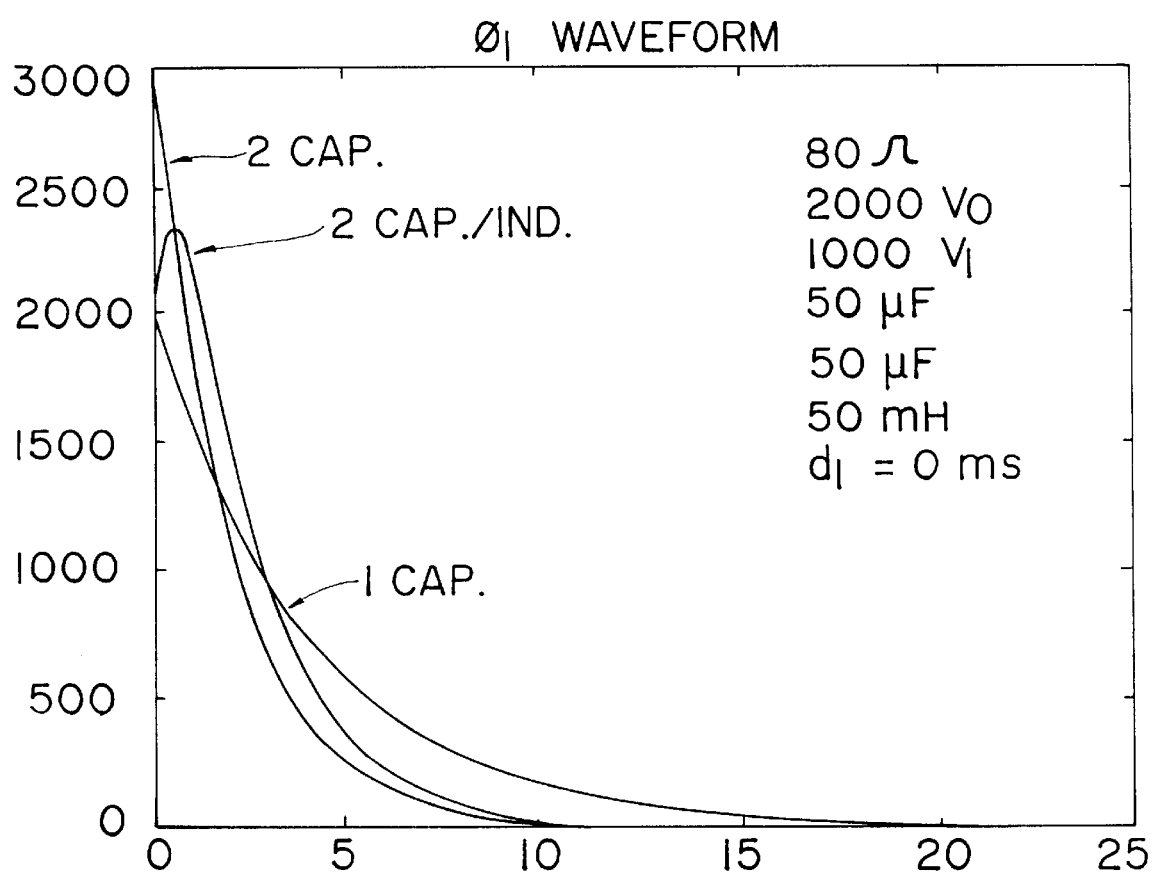
Figure 15C:
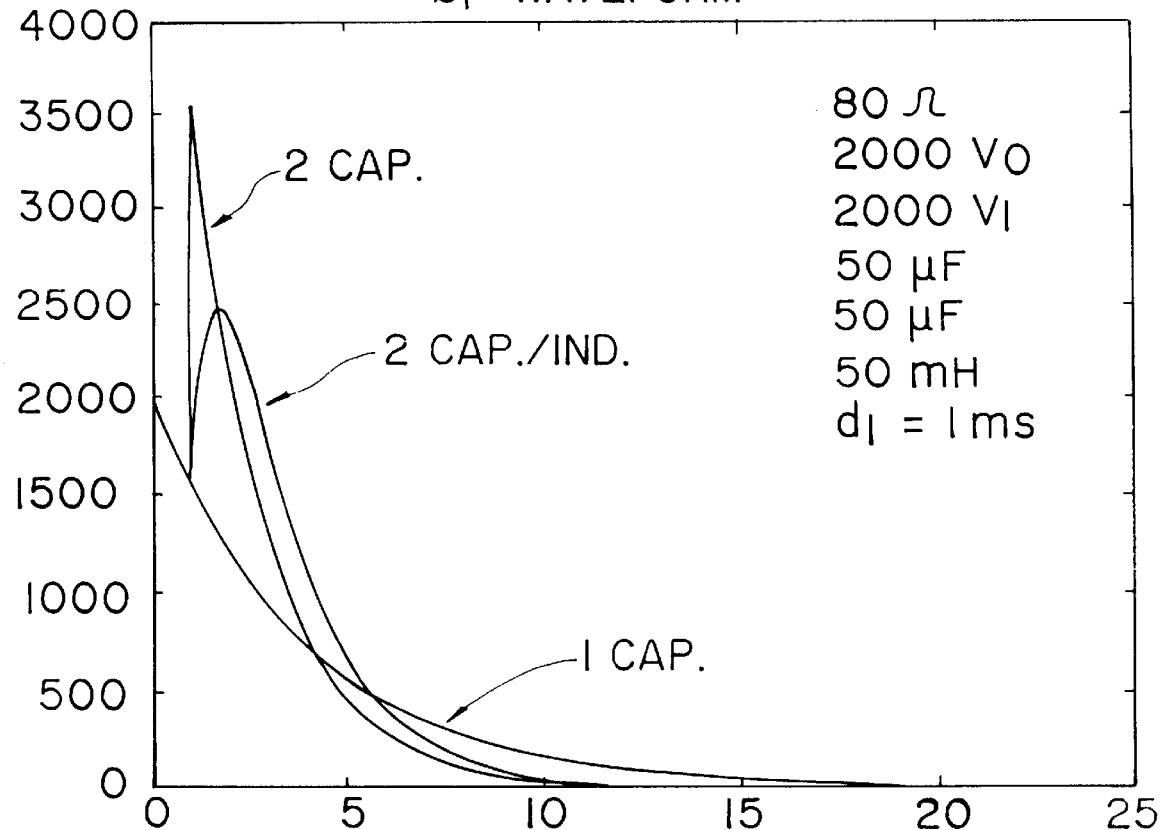

Additional waveforms and cell responses are illustrated in the series of FIGS. 15. FIGS. 15a, 15b, 15c, 15d, 15e, and 15f illustrate comparisons between a single capacitor exponential decay waveform, a double capacitive exponential decay waveform and a stepped capacitor-inductor waveform and associated cell responses for various parameters. The single capacitor waveform and cell response is designated as "1 cap.", the double capacitor waveform and cell response is designated as "2 cap.", and the stepped capacitor/inducer waveform and all response is designated "2 cap./ind.". As illustrated, the stepped capacitor-inductor waveform has the highest and or most effective cell response of the three.

Figure 10:
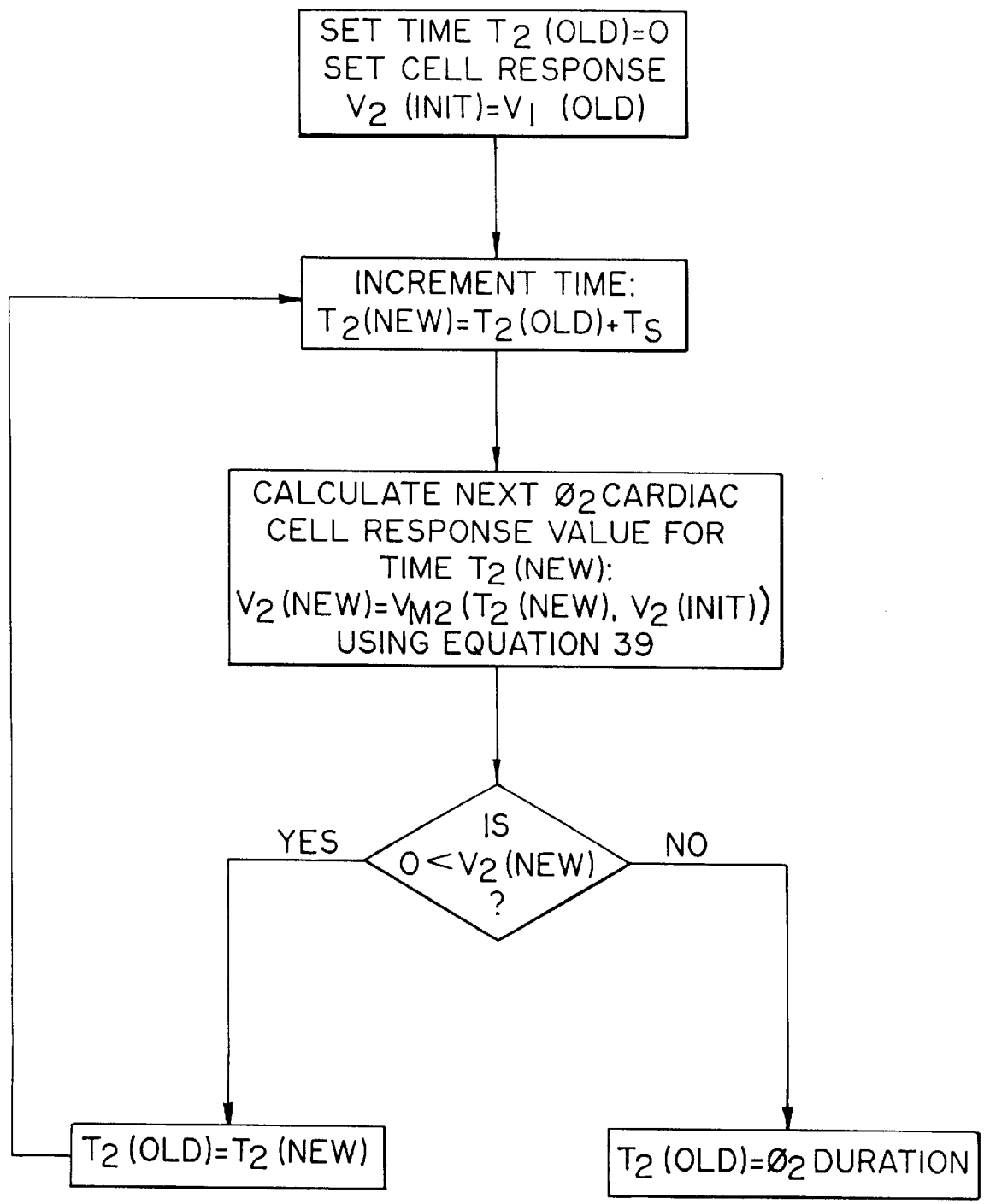
FIG. 10 illustrates a flow chart for the determination and use of the truncation time for $\phi_2$ of the damped sine wave shock pulse.

In the same manner that equation 33 and equation 39 were derived, $\phi_2$ of a biphasic waveform is developed to implement the charge burping design rule. The $\phi_2$ of a shock pulse is required to remove the residual charge remaining on a cardiac cell if that cell did not depolarize due to $\phi_1$ of the shock pulse. As a next step in this process, the cell response to a stepped capacitor damped sine wave implementation of $\phi_2$ is $$V_{M2}(t) = (V_{M1}(d_2)e^{-t/\tau_M}) - L_{21}\left(e^{-t/\tau_L} - e^{(-t/\tau_M)\left(1-\frac{1}{\Omega_M}\right)}\right) - \quad (48)$$

$$L_{22}\left(e^{-t/\tau_C} - e^{(-t/\tau_M)\left(1-\frac{1}{\Omega_M}\right)}\right),$$

where $$L_{21} = \left[\frac{V_S(d_{\phi 1}) - V_0\left(\frac{\tau_C}{\tau_C - \tau_L}\right)}{\Omega_S}\right]\left(\frac{\tau_L}{\tau_C\left(1-\frac{1}{\Omega_M}\right)-\tau_M}\right) \quad (49)$$

and $$L_{22} = \left[\frac{V_0}{\Omega_S}\right]\left(\frac{\tau_C}{\tau_C - \tau_L}\right)\left(\frac{\tau_C}{\tau_C\left(1-\frac{1}{\Omega_M}\right)-\tau_M}\right), \quad (50)$$

where $d\phi_1$ is the total duration of $\phi_1$ of the biphasic shock pulse and $\tau_C$ and $\tau_M$, $\Omega_S$ and $\Omega_M$ are defined in accordance with defibrillation circuitry that implements the stepped capacitor damped sine wave as $\phi_2$ of a biphasic shock pulse. FIG. 10 describes the implementation the charge burping design rule, which is operated prior to the discharge of a $\phi_2$ of a biphasic waveform. The design rule is independent of any implementation of $\phi_1$ of a biphasic shock pulse. The effects of $\phi_1$ on the cardiac cell are incapsulated in the $V_{M1}(t)$ and $V_S(t)$ elements of equations 48, 49, and 50.

Embodiments of the invention apply a waveform that defibrillates the heart based on models of cell response, and which truncates a monophasic waveform of $\phi_1$ of a biphasic waveform at the peak or approximate peak cell response time. As desired, the embodiments of the invention further apply a second phase of a waveform that further defibrillates the heart based on models of the cell response, and which truncates $\phi_2$ of a biphasic waveform at the time a cell response is reset to the cell's natural resting state.

It should be stressed and understood that $\phi_2$ is independent from $\phi_1$. In order to design an effective $\phi_2$ waveform, the only thing needed from $\phi_1$ is to know where the cell response was left when $\phi_1$ truncated. Phase one may be designed based on the truncated damped sine wave equations given above, while $\phi_2$ may be designed and implemented utilizing other technology such as single capacitor for discharge technology and vice-versa. The corresponding design rules for a $\phi_1$ circuitry may be used in conjunction with the design rules for a $\phi_2$ circuitry, regardless of the specific circuitry used to implement each phase of a monophasic or biphasic shock pulse.

Description of Present Invention

Method and apparatus embodiments of a stacked-capacitor defibrillator according to the present invention will now be described, with respect to FIGS. 16–21.

Many damped-sine-wave defibrillation devices and methods require relatively large capacitors and/or inductors, and associated mechanical relays, to function effectively. According to the invention, on the other hand, a damped sine wave is simulated, by "stacking" a number of smaller capacitors in series and gating them through e.g. a solid state control device. The various disadvantages associated with large capacitors and inductors are thus eliminated according to the invention, because capacitor size can be dramatically reduced and inductors eliminated entirely. The likelihood of harm to the heart due to application of excessive charge is also reduced, because voltage increases are sequential instead of instantaneous.

FIG. 16 illustrates a stacked-capacitor defibrillator 200 according to one embodiment of the invention. Defibrillator 200 generates first- and/or second-phase pulse components of defibrillation waveforms that emulate or approximate the truncated sinusoidal waveforms and waveform portions described above. Defibrillator 200 includes a plurality of charge storage devices, such as capacitors $C_1$, $C_2$, ... $C_n$, $C_{n+1}$, and circuits or devices represented by switches $S_1$, $S_2$, ... $S_n$, $S_{n+1}$, interconnected in a series circuit between a pair of electrode terminals $E_1$ and $E_2$. The nodes between each capacitor $C_1$, $C_2$, ... $C_n$, $C_{n+1}$ are connected to electrode terminal $E_2$ by diodes $D_1$–$D_n$, respectively. Switches $S_1$, $S_2$, ... $S_n$, $S_{n+1}$ are coupled to and independently controlled by pulse controller 210 to initiate, control the shape of and truncate (terminate) the defibrillation pulse components. Thus, controller 210 and switches $S_1$, $S_2$, ... $S_n$, $S_{n+1}$ are operatively coupled together as a control apparatus to sequentially interconnect the capacitors in a circuit to generate the desired waveform.

Figure 16A:
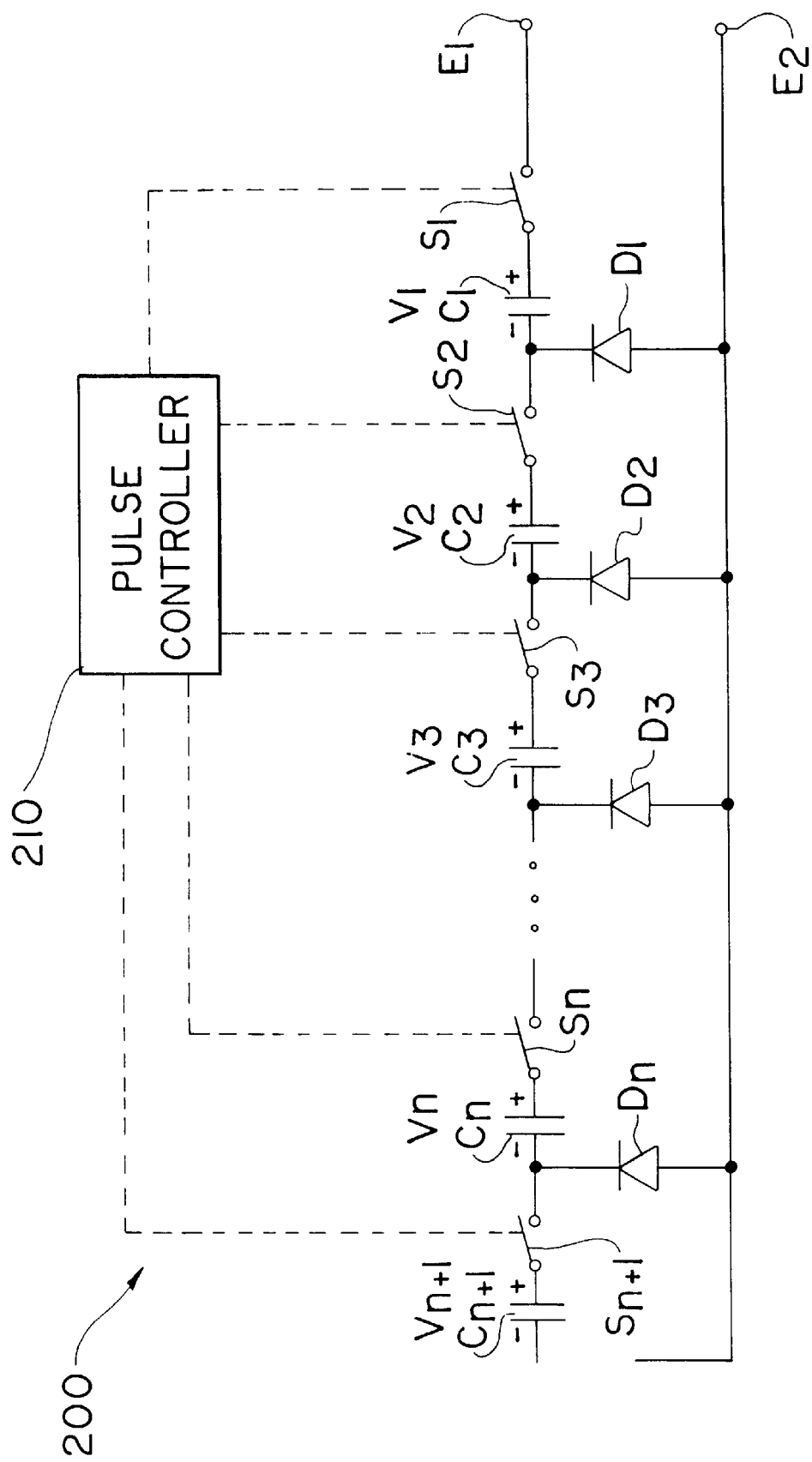
FIG. 16A shows at least a portion of a stacked-capacitor external defibrillation circuit according to an embodiment of the present invention.

The apparatus illustrated in FIG. 16A is constructed to generate one phase component, for example a first-phase component of a defibrillation waveform. The opposite-phase pulse component can be generated by a circuit that is identical to that shown in FIG. 16A and coupled to electrodes $E_1$ and $E_2$ in parallel with the circuit shown in FIG. 16A, thereby providing the means to charge and discharge a biphasic defibrillation shock pulse.

FIG. 16B illustrates a stacked-capacitor waveform that can be produced by the FIG. 16A device and that emulates the first-phase components of the truncated sinusoidal waveforms shown and described above. To generate first-phase pulse component $P_1$, capacitors $C_1$, $C_2$, ... $C_n$, $C_{n+1}$ are charged to their desired first polarity charge potentials. Each of the capacitors, or certain ones of the capacitors, can be charged to a different charge potential as desired for a particular application or patient.

At time $t_0$, as shown, pulse controller 210 causes the circuit elements forming switch $S_1$ to switch to a closed state, initiating a first emulating section of pulse $P_1$. After the first emulating section rises to its peak value it will decay at an exponential rate. At time $t_1$, pulse controller 210 switches switch $S_2$ to a closed state to initiate a second emulating section of pulse component $P_1$. This procedure is repeated by pulse controller 210 through the switching of switch $S_{n+1}$ to its closed state, to initiate the final emulating section. At a predetermined time after switch $S_{n+1}$ is closed, pulse controller 210 can truncate pulse component $P_1$ by switching all switches $S_1$, $S_2$, ... $S_n$, $S_{n+1}$ to an open state. Although not shown, pulse controller 210 can also truncate pulse component $P_1$ by circuitry that rapidly discharges capacitors $C_1$, $C_2$, ... $C_n$, $C_{n+1}$.

The degree to which the stacked-capacitor waveform shown in FIG. 16B follows or approximates a desired pulse-component shape can be controlled in a number of ways, for example by selecting the capacitance values of capacitors $C_1$, $C_2$, ... $C_n$, $C_{n+1}$, the charge potentials $V_1$, $V_2$, ... $V_n$, $V_{n+1}$ to which the capacitors are charged, the times $t_1$, $t_2$, ... $t_n$, $t_{n+1}$ at which switches $S_1$, $S_2$, ... $S_n$, $S_{n+1}$ are switched to a closed state, and the number n of the states of the capacitors and the switches.

Figure 17B:
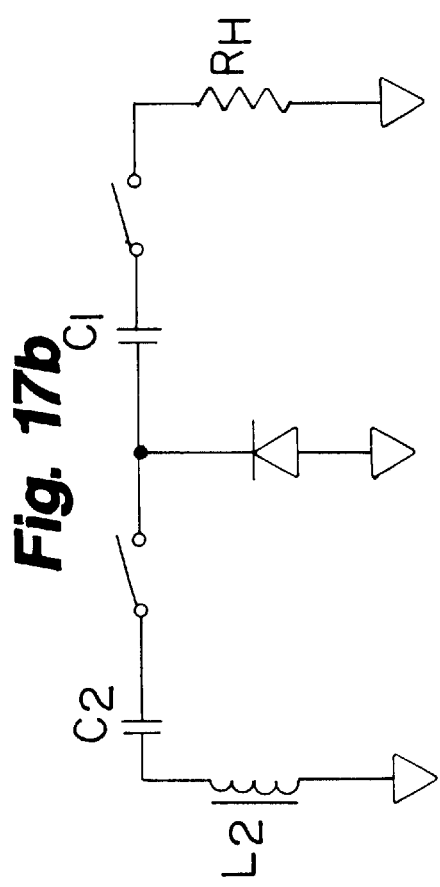
FIGS. 17B–17C show at least portions of stacked-capacitor external defibrillation circuits according to embodiments of the invention.
Figure 17C:
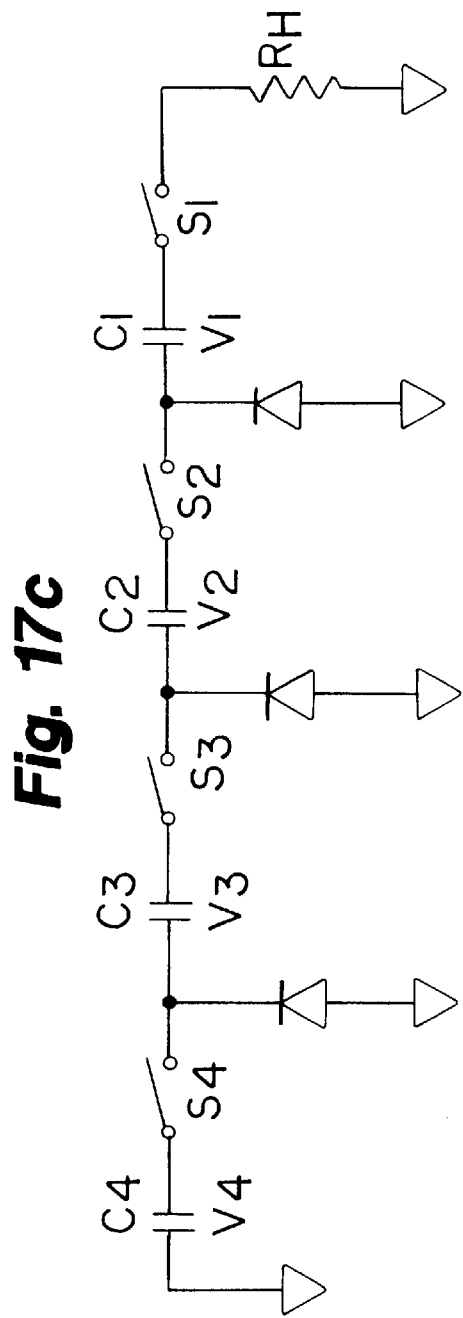

In a similar manner, the circuit shown in FIG. 17C and corresponding defibrillation pulse $A_2$ (FIG. 17A) can be used to generate emulated versions of the truncated stepped sinusoidal defibrillation circuit and pulse $A_1$ shown in FIGS. 17A and 17B.

Figure 14:
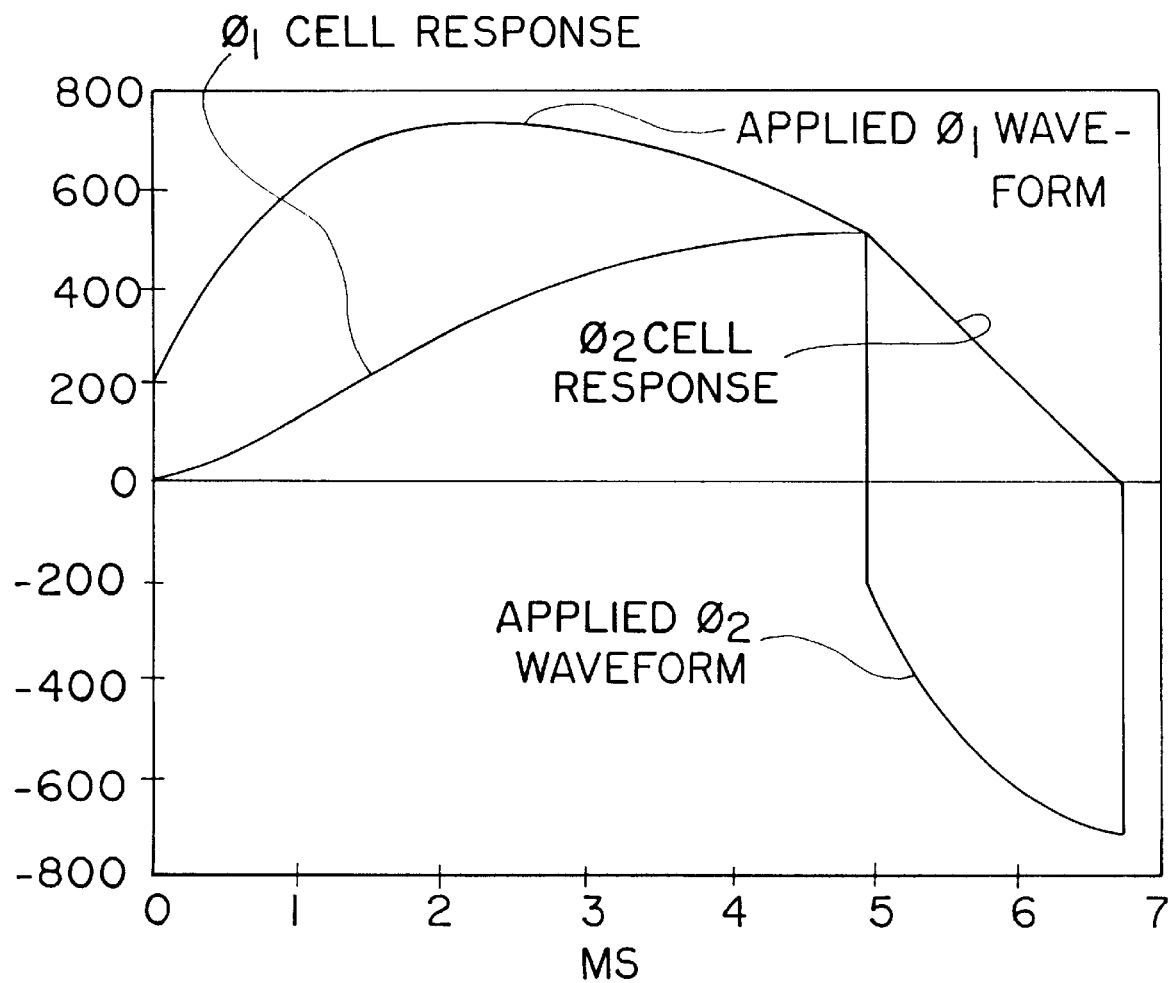
FIG. 14 is an illustration of a biphasic stepped capacitor truncated damped sinusoidal waveform and its associated cell membrane response.
Figure 18A:
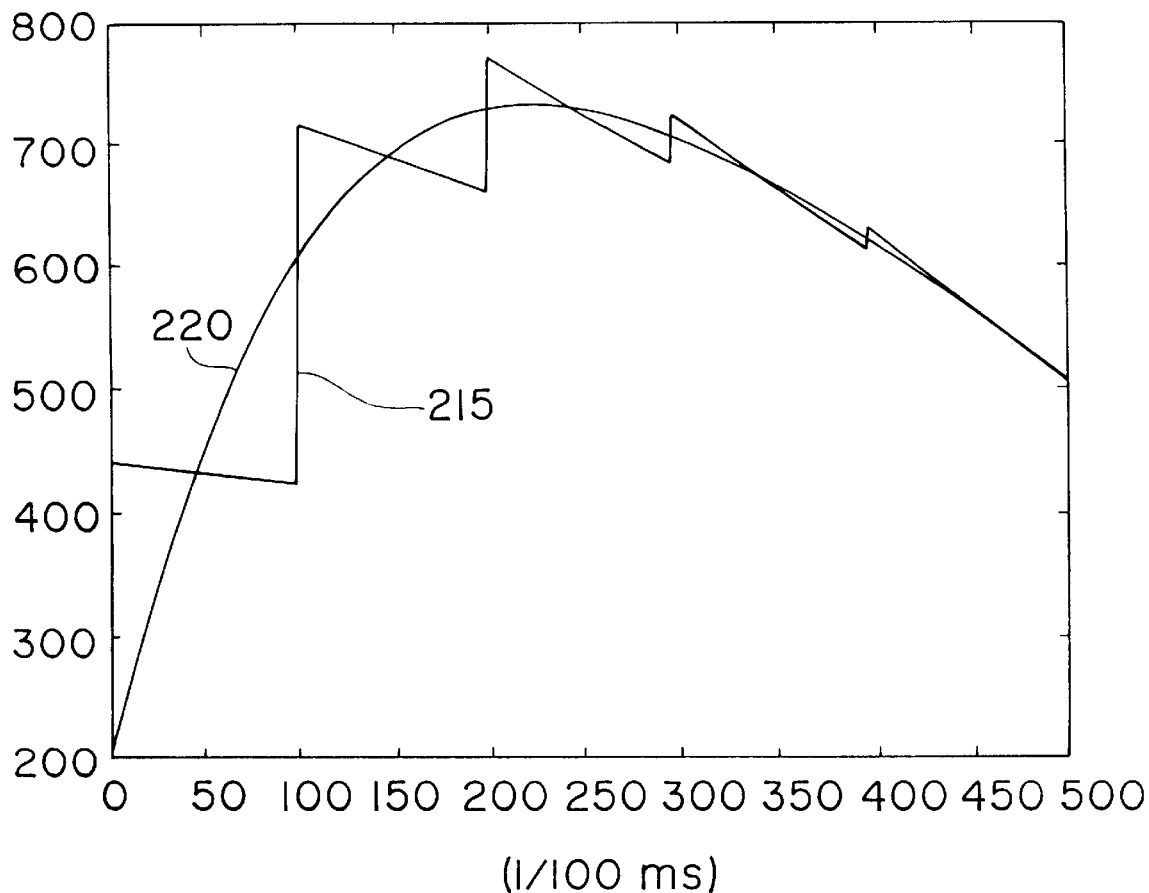
FIG. 18A shows a stepped waveform according to an embodiment of the invention.
Figure 18B:
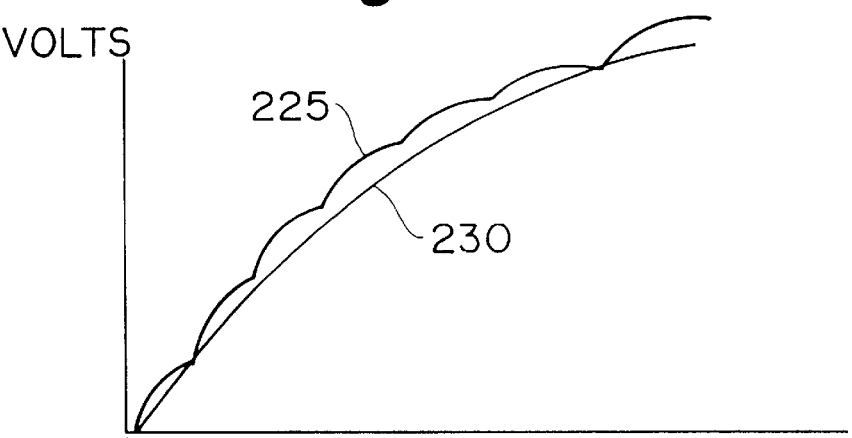
FIG. 18B shows cell-response curves according to an embodiment of the invention.
Figure 19:
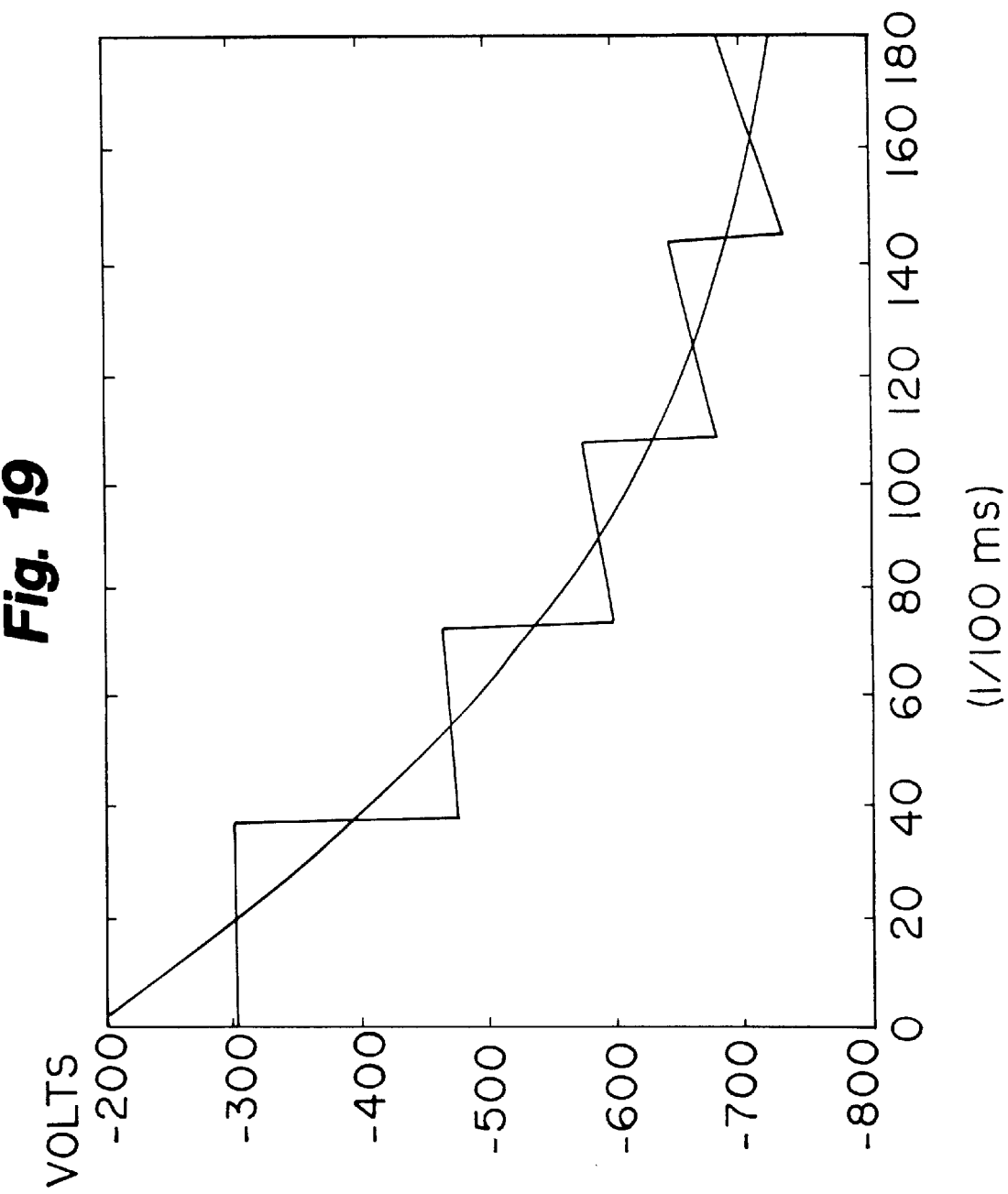
FIGS. 19–20 show stepped waveforms according to embodiments of the invention.
Figure 20:
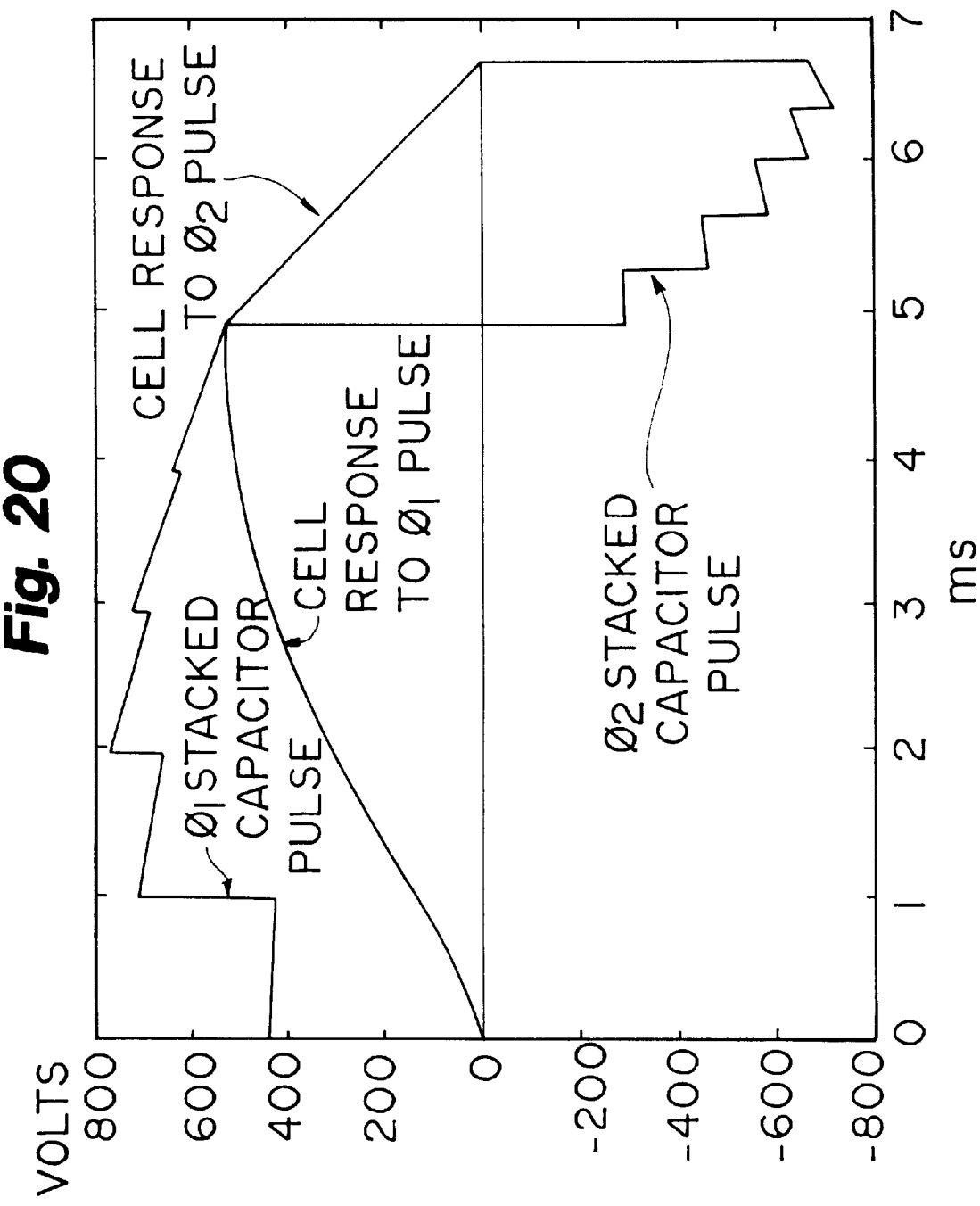

FIGS. 18–20 illustrate how the waveform of FIG. 14, described with respect to previous embodiments, can be approximated using stacked-capacitor devices and methods to achieve substantially similar cell response. A first-phase waveform 215 achievable using a five-capacitor embodiment according to the invention is shown in FIG. 18A. As successive capacitors are switched in, stacked-capacitor waveform 215 jumps to a corresponding extent, followed by corresponding decay. Waveform 215 thus substantially follows the FIG. 14 waveform, illustrated in FIG. 18A at 220. Cell response to stacked-capacitor waveform 215, shown in greatly exaggerated form at 225 in FIG. 18B for purposes of illustration, closely approximates cell response achievable with a more traditional damped sine waveform, illustrated at 230. FIG. 19 illustrates a corresponding second-phase waveform, and FIG. 20 shows both the first-phase and second-phase waveforms together and the corresponding cell response. As will be apparent, the FIG. 20 cell response is similar to that of FIG. 14. Further aspects of cell response achievable according to the invention will be described below.

The theory behind the stacked-capacitor embodiments of the invention, as well as several theoretical examples, will now be described.

Define:

$$\tau_n = R \cdot C_n \tag{51a}$$

$$n=1: C_1 = C_1 \tag{51b}$$

$$n \geq 2: C_n = \frac{C_n \cdot C_{n-1}}{C_n + C_{n-1}} \tag{51c}$$

Assume all switches $S_n$ are open.

Stage 1

$V_1 = V_1$, where $V_1$ is the initial voltage on capacitor $C_1$ $\tau_1 = R \cdot C_1 = R \cdot C_1$ Let switch $S_1$ close. Then a capacitive discharge occurs, so that at time $d_1$, the duration of the discharge, capacitor $C_1$ has voltage equal to:

$$\text{Voltage} = V_1 e^{-d_1/\tau_1} \tag{52}$$

Stage 2

Immediately following the duration $d_1$, switch $S_2$ is closed. Then switch $S_1$ and $S_2$ implement a capacitive discharge of two capacitors in series. If $V_2$ is the initial voltage on capacitor $C_2$, then the total voltage at $d_1$ becomes:

$$V_2 = V_1 e^{-d_1/\tau_1} + V_2 \tag{53}$$

If the discharge proceeds for a time of $d_2$ and until time $d = d_1 + d_2$, then the voltage remaining on the series combination of $C_1$ and $C_2$ is $$V_2 e^{-d_2/\tau_2} \tag{54}$$

where $\tau_2$ is defined above.

Stage n

Immediately following the duration $d_{n-1}$ (from stage n–1), switch $S_n$ is closed. Then switches $S_1, \ldots, S_n$ implement a capacitive discharge of n capacitors in series. If $V_n$ is the initial voltage on capacitor $C_n$, then the total voltage at $d = d_1 + \ldots + d_{n-1}$ is:

$$V_n = V_{n-1} e^{(-d_{n-1})/(\tau_{n-1})} + V_n \tag{55}$$

If the discharge proceeds for a time of $d_n$ and until time $d = d_1 + \ldots + d_n$, then the voltage remaining on the series combination of $C_1, \ldots, C_n$ is:

$$V_n e^{-d_n/\tau_n} \tag{56}$$

As described in equation 26, and assuming $V_G = 0$, the cardiac cell response to stage 1 is:

$$V_{MI}(d_1) = V_1 \cdot \tau_1^* \cdot \left( e^{-d_1/\tau_1} - e^{\left(\frac{-d_1}{\tau_M}\right)\left(1 - \frac{1}{\Omega_M}\right)} \right) \tag{57}$$

where $$\tau_1^* = \left(\frac{1}{\Omega_s}\right) \left( \frac{\tau_1}{\tau_1\left(1 - \frac{1}{\Omega_M}\right) - \tau_M} \right)$$

with $\tau_1$, $d_1$ defined as above. At Stage 2, the cumulative cardiac cell response is:

$$V_{M2}(d_2) = V_2 \cdot \tau_2^* \cdot \left( e^{-d_2/\tau_2} - e^{\left(\frac{-d_2}{\tau_M}\right)\left(1-\frac{1}{\Omega_M}\right)} \right) \quad (58)$$

with $$\tau_2^* = \left(\frac{1}{\Omega_s}\right)\left|\frac{\tau_2}{\tau_2\left(1-\frac{1}{\Omega_M}\right)-\tau_M}\right|$$

with $\tau_2$, $d_2$ defined as above.

Therefore, at the end of stage n, the cumulative cardiac cell response is:

$$V_{Mn}(d_n) = V_n \cdot \tau_n^* \cdot \left( e^{-d_n/\tau_n} - e^{\left(\frac{-d_n}{\tau_M}\right)\left(1-\frac{1}{\Omega_M}\right)} \right) \quad (59)$$

with $$\tau_n^* = \left(\frac{1}{\Omega_s}\right)\left|\frac{\tau_n}{\tau_n\left(1-\frac{1}{\Omega_M}\right)-\tau_M}\right|$$

with $\tau_n$, $d_n$ defined as above.

In this manner, a stacked-capacitor circuit according to embodiments of the invention is implemented. It is clear from FIGS. 18–20 that the stacked-capacitor circuit approximates any waveform that is developed as a defibrillation shock pulse.

For illustrative purposes below, it will be assumed that the capacitance for each capacitor in the bank of capacitors for the stacked-capacitor circuitry is the same. That is, $C_1=C_2=\ldots=C_n$. It is also assumed that the stage durations $d_i$ are the same. That is, each stage, and therefore the current delivered during that stage, has a fixed duration, so that $d_1=d_2=\ldots=d_n$, and hence $d=nd_1$.

It will be clear from the description of the preferred embodiments that methods and devices according to the invention are not limited by these assumptions. These assumptions are illustrative and simplify the presentation and explanation herein below.

Given a general defibrillation waveform, denoted by F, then the waveform takes on some characteristic shape and is defined as set forth below:

(60A) F is continuous on (0, d)

(60B) F(t)=0

(60C) F(t)≧0, 0≦t≦d where d represents duration of the shock pulse described by F. Suppose also that the duration d is divided into one or more segments $d_1, d_2, \ldots, d_n$ so that $n \geq 1$, $d_1=d_2=\ldots=d_n$, and $d=d_1+d_2+\ldots+d_n$. Suppose also that the capacitance values for each capacitor are the same, so that $C=C_1=C_2=\ldots=C_n$. The number of capacitor stages $C_i$ equals the number of time segments, $d_i$.

Let G(t) represent the waveform created by a stacked-capacitor defibrillator circuit. The formulation set forth below determines the optimal voltage values $V_i$ placed on the capacitors $C_i$, i=1, 2, . . . , n, so that the waveform F(t) is best approximated. The optimizing constraints are:

$$\int_0^d F(t)dt \doteq \int_0^d G(t)dt \quad (61)$$

and $$\int_{d_{k-1}}^{d_k} F(t)dt \doteq \int_{d_{k-1}}^{d_k} G(t)dt, \text{ for } k=1,\ldots,n. \quad (62)$$

These constraints state that the area under the curves for F and for G must be the same area, and that further, the area under the curve for each stage of the waveform delivered from the stacked-capacitor circuit must be equal to the area under the curve for F(t) during the time of that stage. Recall that a stage of the stacked-capacitor defibrillator is defined by switch $S_k$ closing at the start of the stage and no additional switches $S_{k+1}, \ldots, S_n$ close for a duration of the $d_k$, k=1, . . . , n.

At the nth stage, the stacked-capacitor waveform G(t) may be written as $$G_n(t) = V_n e^{-t/\tau_n} \quad (63)$$

where $t \in [0, d_n]$ and $\tau_n = R_1 \cdot C_n$ as defined above.

Therefore, $$\int_0^d G(t)dt = \sum_{n=1}^N \int_0^T G_n(t)dt \quad (64)$$

where T is the predetermined duration of each stage and N is the total number of stages. Then $$\int_0^d G = \sum_{n=1}^N \int_0^T G_n = \sum_{n=1}^N (V_n \cdot \tau_n \cdot (1-e^{-T/\tau_n})) \quad (65)$$

where $$\int_o^T G_n = -V_n\tau_n e^{-t/\tau_n}\big]_o^T = V_n \cdot \tau_n \cdot (1-e^{-T/\tau_n}) \quad (66)$$

and $$V_n = V_{n-1} e^{-T/(\tau_{n-1})} + V_n. \quad (67)$$

Without further knowledge of F(t), the integration of F can be rewritten in the same manner as G, so that $$\int_0^d F = \sum_{n=1}^N \int_{d_{n-1}}^{d_n} F \quad (68)$$

where $d_0=0$ and $d_N=d$. Then denote $$\int_{d_{n-1}}^{d_n} F = F_n.$$

Then the constraints demand that $$F_n = V_n \cdot \tau_n \cdot (1-e^{-T/\tau_n}). \quad (69)$$

Then $$V_n = \frac{F_n}{\tau_n \cdot (1 - e^{-T/\tau_n})} \tag{70}$$

or $$V_{n-1} e^{-T/\tau_{n-1}} + V_n = \frac{F_n}{\tau_n \cdot (1 - e^{-T/\tau_n})} \tag{71}$$

Therefore, the defining equation for voltage at the nth stage is:

$$V_n = \frac{F_n}{\tau_n (1 - e^{-T/\tau_n})} - V_{n-1} e^{-T/\tau_{n-1}} \tag{72}$$

Then, for a three capacitor system, for example, $$V_1 = \frac{\int_0^T F(t)dt}{\tau_1 (1 - e^{-T/\tau_1})},$$

$$V_2 = \frac{\int_T^{2T} F(t)dt}{\tau_2 (1 - e^{-T/\tau_2})} - V_1 e^{-T/\tau_1},$$

and $$V_3 = \frac{\int_{2T}^{3T} F(t)dt}{\tau_3 (1 - e^{-T/\tau_3})} - (V_1 e^{-T/\tau_1} + V_2) e^{-T/\tau_2}$$

As an example of a waveform for F(t), the truncated damped sine waveform may be used as an illustrative example, which is equation 14B, so that:

$$F(t) = V_{DS} \frac{\tau_{CI}}{\tau_{CI} - \tau_{LI}} (e^{-t/\tau_{CI}} - e^{-t/\tau_{LI}})$$

for $0 \leq t \leq d$ and $V_{DS}$=initial voltage on the damped sine wave capacitor, where d is the predetermined duration for the damped sine shock pulse. Then $$\int_{T_1}^{T_2} F(t)dt = V_{DS} \left(\frac{\tau_{CI}}{\tau_{CI} - \tau_{LI}}\right) \left[\int_{T_1}^{T_2} e^{-t/\tau_{CI}} dt - \int_{T_1}^{T_2} e^{-t/\tau_{LI}} dt\right],$$

where $$\int_{T_1}^{T_2} e^{-t/\tau} dt = \tau (e^{-T_1/\tau} - e^{-T_2/\tau}).$$

Then the three capacitor implementation for a stacked-capacitor shock pulse that approximates the truncated damped sine wave is defined by $d_1 = d_2 = d_3 = T$, and $C_1 = C_1 = C_2 = C_3 = C$, and $$V_1 = \frac{V_{DS}\left(\frac{\tau_{CI}}{\tau_{CI} - \tau_{LI}}\right)[\tau_{CI}(1 - e^{-T/\tau_{CI}}) - \tau_{LI}(1 - e^{-T/\tau_{LI}})]}{\tau_1 (1 - e^{-T/\tau_1})}$$

$$V_2 = \frac{V_{DS}\left(\frac{\tau_{CI}}{\tau_{CI} - \tau_{LI}}\right)\left[\tau_{CI}(e^{-T/\tau_{CI}} - e^{-2T/\tau_{CI}}) - \tau_{LI}\left(e^{\frac{-T}{\tau_{LI}}} - e^{\frac{-2T}{\tau_{LI}}}\right)\right]}{\tau_2 (1 - e^{-T/\tau_2})} - V_1 e^{-T/\tau_1}$$

and $$V_3 = \frac{V_{DS}\left(\frac{\tau_{CI}}{\tau_{CI} - \tau_{LI}}\right)\left[\tau_{CI}\left(e^{\frac{-2T}{\tau_{CI}}} - e^{\frac{-3T}{\tau_{CI}}}\right) - \tau_{LI}\left(e^{\frac{-2T}{\tau_{LI}}} - e^{\frac{-3T}{\tau_{LI}}}\right)\right]}{\tau_3 \left(1 - e^{\frac{-T}{\tau_3}}\right)} - \left(V_1 e^{\frac{-T}{\tau_1}} + V_2\right) e^{\frac{-T}{\tau_2}}$$

As an illustrative example, a stacked capacitor defibrillation circuit is designed to take the place of a more cumbersome but clinically important defibrillation circuit that delivers a biphasic truncated stepped-capacitor damped sine waveform. Referring to FIG. 17B, the stepped-capacitor damped sine circuit is implemented such that $C_1$ is a 50 $\mu$F capacitor charged to 200 V, $C_2$ is a 50 $\mu$F capacitor charged to 2000V, $L_2$ is a 250 mH inductor, and it is assumed that the shock pulse will be delivered into an 80$\Omega$ load. This biphasic waveform is described as $A_1$ in FIG. 17A.

The stacked-capacitor shock pulse is designed such that there are five 300 $\mu$F capacitors. Each switch following switch S1 will be closed, in order, every 1 ms. The initial voltages for the five capacitors are determined using equations (63)–(72). The voltages are $V_1$=440 V, $V_2$=292 V, $V_3$=113 V, $V_4$=41 V, and $V_5$=17 V, according to this embodiment. Of course, other embodiments may use different values. For phase two ($\phi_2$), the same circuit is duplicated for the $\phi_2$ bank, as is illustrated in FIG. 5B for a second phase to a biphasic waveform. The $\phi_2$ circuit would again have five 300 $\mu$F capacitors switching into delivery at 1 ms intervals, and have initial voltages of $V_1$=303 V, $V_2$=177 V, $V_3$=137 V, $V_4$=109 V, and $V_5$=91 V. The resulting $\phi_1$ shock pulse is shown in FIGS. 18A and 20. It is clear that the stacked-capacitor waveform closely approximates the stepped-capacitor damped sine waveform. Further, the resulting $\phi_2$ shock pulse is shown in FIGS. 19 and 20, and the final combination of $\phi_1$ and $\phi_2$ and the associated cell response are shown in FIG. 20.

The criterion to determine the appropriateness for approximation by the stacked-capacitor waveform is its effects on cardiac cell response when compared to the response elicited by the shock pulse being approximated. The cell response to $\phi_1$ of the stacked capacitor waveform is expressed in the shock pulse stages:

For stage 1, $$V_{MI1}(t) = \frac{V_{11}}{\Omega_S}\left(\frac{\tau_{11}}{\tau_{11}\left(1-\frac{1}{\Omega_M}\right)-\tau_M}\right)\left(e^{\frac{-t}{\tau_{11}}} - e^{\frac{-t}{\tau_M}\left(1-\frac{1}{\Omega_M}\right)}\right),$$

where $\tau_{11}=R \cdot C_{11}$ and $V_{11}$ is the initial voltage, and $C_{11}$ is the first capacitor of $\phi_1$ of the stacked-capacitor waveform.
For stage 2, $$V_{MI2}(t) = \frac{V_{12}}{\Omega_S}\left(\frac{\tau_{12}}{\tau_{12}\left(1-\frac{1}{\Omega_M}\right)-\tau_M}\right)\left(e^{\frac{-t}{\tau_{12}}} - e^{\frac{-t}{\tau_M}\left(1-\frac{1}{\Omega_M}\right)}\right) +$$

$$V_{MI1}(d_{11})e^{\frac{-t}{\tau_M}\left(1-\frac{1}{\Omega_M}\right)}$$

where $\tau_{12}=R \cdot C_{12}$, $d_{11}$ is the duration of stage 1, $V_{M11}(d_{11})$ is the cell membrane voltage at the end of the first stage, $V_{12}$ is the initial voltage, and $C_{12}$ is the second capacitor of $\phi_1$ of the stacked-capacitor waveform.
For stage k:

$$V_{MIk}(t) = \frac{V_{1k}}{\Omega_S}\left(\frac{\tau_{1k}}{\tau_{1k}\left(1-\frac{1}{\Omega_M}\right)-\tau_M}\right)\left(e^{\frac{-t}{\tau_{1k}}} - e^{\frac{-t}{\tau_M}\left(1-\frac{1}{\Omega_M}\right)}\right) +$$

$$V_{MI(k-1)}(d_{1(k-1)})e^{\frac{-t}{\tau_M}\left(1-\frac{1}{\Omega_M}\right)}$$

where $\tau_{1k}=R \cdot C_{1k}$, $V_{1k}$ is the initial voltage, $C_{1k}$ is the $k^{th}$ capacitor for the $k^{th}$ stage of $\phi_1$, $d_{1(k-1)}$ is the duration for previous stage and $V_{M1(k-1)}(d_{1(k-1)})$ is the cell membrane response at the end of the previous stage.

In the same manner, the $k^{th}$ stage cardiac cell response to the $\phi_2$ portion of a biphasic stacked capacitor waveform is $$V_{M2k}(t) = \left[\frac{V_{2k}}{\Omega_S}\left(\frac{\tau_{2k}}{\tau_{2k}\left(1-\frac{1}{\Omega_M}\right)-\tau_M}\right)\left(e^{\frac{-t}{\tau_M}\left(1-\frac{1}{\Omega_M}\right)} - e^{\frac{-t}{\tau_{2k}}}\right)\right] +$$

$$V_{M2(k-1)}(d_{2(k-1)}) \cdot e^{\frac{-t}{\tau_M}\left(1-\frac{1}{\Omega_M}\right)}$$

where $\tau_{2k}=R \cdot C_{2k}$, $V_{2k}$ is the initial voltage, $C_{2k}$ is the $k^{th}$ stage of $\phi_2$, $d_{2(k-1)}$ is the duration for the previous stage and $V_{M\ 2(k-1)}(d_{2(k-1)})$ is the cell membrane response at the end of the previous $\phi_2$ stage.

Analysis and simulation demonstrate that the constraints that are used to design a stacked-capacitor approximation to a shock pulse are the same constraints that create a cardiac cell response for the stacked-capacitor waveform that matches the response desired from the delivery of the general defibrillation waveform. FIG. 18B illustrates the cell response 230 for $\phi_1$ of a general defibrillation waveform and the cell response 225 of the corresponding stacked-capacitor defibrillation waveform that approximates it. Therefore, the $\phi_1$ and $\phi_2$ durations for the stacked-capacitor waveform are the same durations as the approximated shock pulse. Therefore, the $\phi_1$ and $\phi_2$ durations are predetermined, prior to the discharge of the stacked-capacitor phase, as illustrated in FIGS. 9 and 10. At that time, the $\phi_1$ and $\phi_2$ durations are divided by the number of stages for each phase circuit. If the $\phi_1$ delivery circuit comprises five capacitors, then the duration $d_{\phi 1}$ for phase one is divided by 5, thereby defining the time T for each $\phi_1$ stage, so that by example $$T = \frac{d_{\phi 1}}{n_1},$$

where $n_1$=number of $\phi_1$ stages.

Figure 21A:
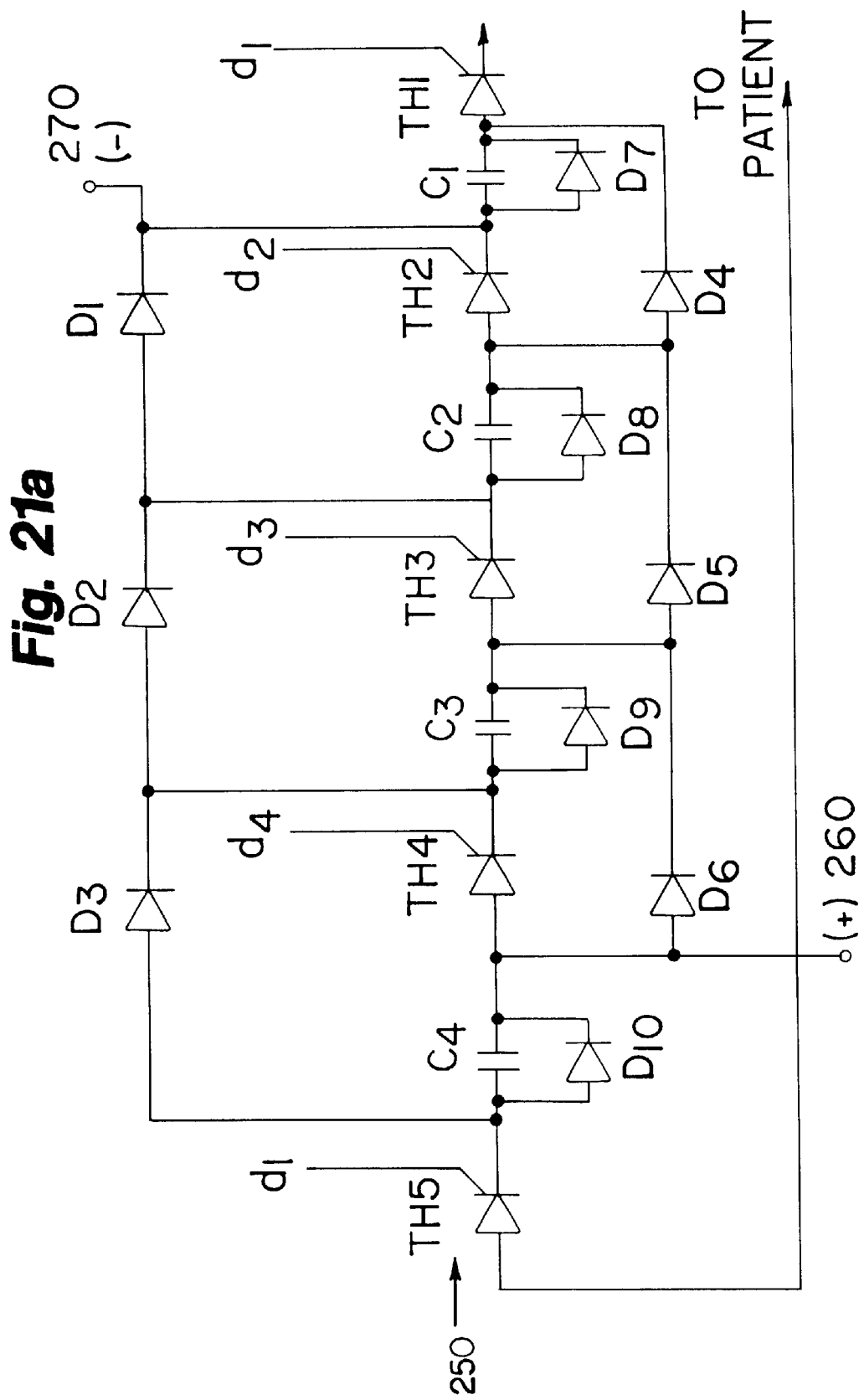
FIG. 21A shows a stacked-capacitor external defibrillation circuit according to an embodiment of the invention.
Figure 21B:
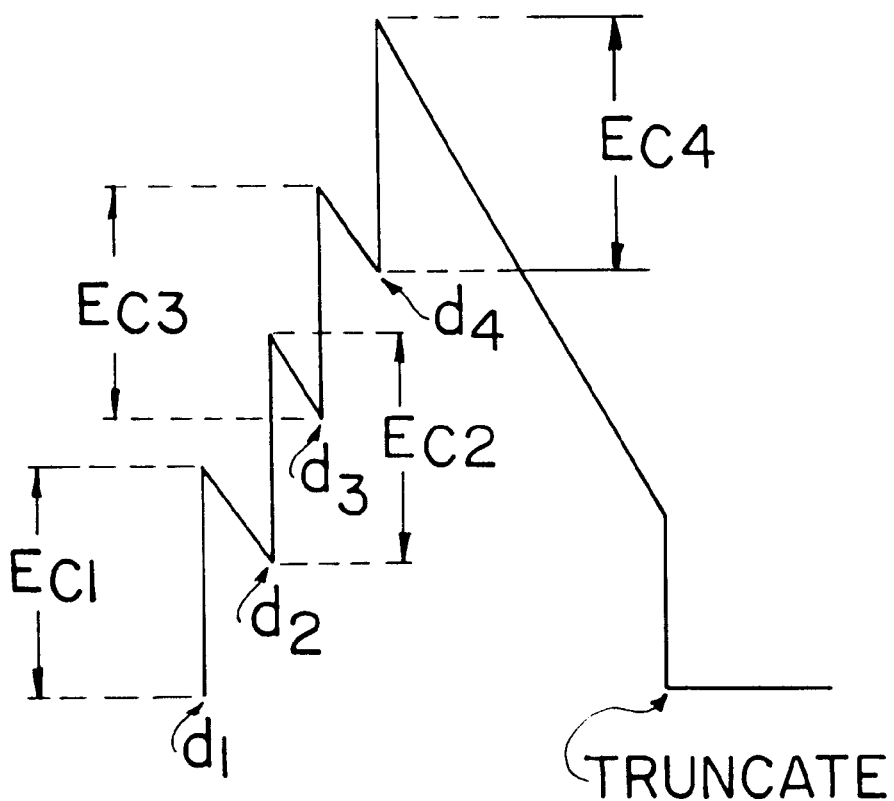
FIG. 21B shows a stepped waveform according to an embodiment of the invention.

The T time value and the circuit parameters for $\phi_1$ are input to equation (72) iteratively to determine the correct voltages on each capacitor. Then each capacitor of $\phi_1$ is charged to the appropriate value, using circuitry described in commonly assigned U.S. patent application Ser. Nos. 08/673,804 and 08/673,195. Additionally, a circuit and waveform according to this embodiment is shown in FIGS. 21A–21B, as will now be described. FIG. 21A is a circuit diagram of a capacitor and diode arrangement, and FIG. 21B is an illustration of the expected output waveform as each successive capacitor is switched into the series connection.

Turning to FIG. 21A, the capacitor bank 250 is charged in parallel by applying charge current to the Charge(+) and Charge(−) terminals 260, 270. Looking at C3, for example, charge current flows from the Charge(−) terminal 270 through D6 to the positive plates of C3. The charging current then flows from the negative plates of C3 through the series connection of diodes D2 and D1 back to the Charge(+) terminal 260. A path similar to this is provided for each of the capacitors and effectively charges them in parallel. No one capacitor will ever have a higher or lower charge voltage than any of the rest. The capacitors may be of radically different capacitance values and still be charged to the same voltage according to this embodiment.

Delivering the energy stored in the capacitors to the patient load occurs by triggering the thyristors in a timed sequence, thereby connecting the capacitors effectively in series, and also connecting the two ends of the stack of capacitors to the patient electrodes. The capacitors are discharged into the patient and the output waveform is a truncated waveform. The truncation can be accomplished by way of an electronic switch in series with the patient, for example. This switch is opened and the current into the patient is interrupted. This interruption allows the thyristors to turn off due to low holding current and the circuit stabilizes in this off state.

According to this embodiment, each of the thyristors is independently controlled. One sequence of operation is to apply trigger pulse d1 to thyristors TH1 and TH5 simultaneously. This causes the charge held in C1 to flow through TH1, through the patient's chest, through TH5, and finally through the string of diodes D3, D2, and D1 back to the negative side of C1. As the current from C1 is flowing, assume that a second trigger pulse is now applied to thyristor TH2. This effectively couples capacitor C2 in series with C1. The voltage of C2 is added to the remaining voltage of C1 and the output voltage is stepped up to the total amount of the sum of the two.

At some time after this event, the trigger pulse is applied to d3, causing thyristor TH3 to be turned on and causing the voltage on capacitor C3 to be added to the voltage of C1 and C2. This sequence can be followed through for all the capacitors in the string, as many as is needed and practical, and the operation is the same. The timing is not necessarily critical, but can advantageously be controlled by a microprocessor. Diodes D7 through D10 will provide a shunt path for the discharge current around its associated capacitor in the event the charge of that capacitor is completely dissipated before the others have completely discharged. The output may be truncated by the same techniques used in the previously described circuit embodiments. FIG. 21B illustrates the output of the circuit, where $E_{C_i}$, for i=1, 2, 3, 4, is the initial voltage on each capacitor $C_i$ illustrated in FIG. 21A.

Similarly, the time T for $\phi_2$ is calculated by $T=d\phi_2/n_2$, where $d\phi_2$ is the calculated $\phi_2$ duration (FIG. 10) and $n_2$ is the number of capacitor stages for the $\phi_2$ embodiment of the biphasic stacked-capacitor shock pulse. Using equation (72) iteratively, the voltages for the capacitor stage are determined, and the capacitors are charged. At this time, the biphasic stacked-capacitor defibrillation circuitry delivers the shock pulse to the patient. The biphasic stacked capacitor waveform is illustrated in FIGS. 18–20. The illustrated waveform is implemented according to the five-stage example described above.

Although the present invention has been described with reference to preferred embodiments, workers skilled in the art will recognize that changes may be made in form and detail without departing from the spirit or scope of the present invention.

What is claimed:

1. Apparatus for generating a waveform, the waveform for use in externally defibrillating the heart of a patient, the apparatus comprising:
   a plurality of capacitors chargeable to respective charge potentials;
   at least one charging device operably coupled to the plurality of capacitors for charging the plurality of capacitors to the respective charge potentials; and
   control apparatus operatively coupled with the capacitors to sequentially interconnect the capacitors in a circuit with one another to generate one phase of a waveform, the waveform comprising an emulated first-phase substantially sinusoidally shaped pulse component having a first polarity, the control apparatus being constructed to truncate the emulated first-phase pulse component at a predetermined time based on a design rule used to calculate pulse duration, the design rule calculating the pulse duration to correspond to substantially the peak response of the patient's heart-cell membrane to the first-phase pulse component.

2. The apparatus of claim 1, wherein the control apparatus is constructed to interconnect the capacitors in a series circuit with one another.

3. The apparatus of claim 1, wherein the waveform is biphasic.

4. The apparatus of claim 3, wherein the biphasic waveform comprises an emulated second-phase substantially sinusoidally shaped pulse component having a second polarity.

5. The apparatus of claim 1, wherein the control apparatus includes a microprocessor.

6. The apparatus of claim 1, wherein the control apparatus includes at least one switch.

7. The apparatus of claim 6, wherein the structure operatively coupled with the capacitors and the control apparatus to apply the waveform to the chest of the patient includes at least two electrodes.

8. The apparatus of claim 1, further comprising structure operatively coupled with the capacitors and the control apparatus to apply the waveform to the chest of the patient.

9. Apparatus for generating a waveform, the waveform for use in externally defibrillating the heart of a patient, the apparatus comprising:
   capacitor means for being charged to respective charge potentials, the capacitor means comprising a plurality of capacitors; and
   control means operatively coupled with the capacitor means for sequentially interconnecting capacitors of the capacitor means in a circuit with one another to generate one phase of a waveform, the waveform comprising an emulated first-phase substantially sinusoidally shaped pulse component having a first polarity, the control means truncating the emulated first-phase pulse component at a predetermined time based on a design rule used to calculate pulse duration, the design rule calculating the pulse duration to correspond to substantially the peak response of the patient's heart-cell membrane to the first-phase component.

10. The apparatus of claim 9, wherein the waveform is biphasic.

11. The apparatus of claim 10, wherein the waveform comprises an emulated second-phase substantially sinusoidally shaped pulse component having a second polarity.

12. The apparatus of claim 9, wherein the control means comprises means for switching the capacitor means into and/or out of the circuit.

13. The apparatus of claim 9, further comprising means operatively coupled with the capacitors and the control apparatus for applying the waveform to the chest of the patient.

14. The apparatus of claim 9, wherein the control means further is operatively coupled with the capacitor means for sequentially interconnecting capacitors of the capacitor means in a circuit with one another to generate a second phase of a waveform.

15. A method of generating a waveform for use in externally defibrillating the heart of a patient, the method comprising:
   (a) charging a plurality of capacitors to charge potentials; and
   (b) sequentially interconnecting the capacitors in a circuit with one another to generate one phase of a waveform;
   wherein step (b) includes generating a first-phase sinusoidally shaped pulse component having a first polarity and truncating the emulated first-phase pulse component at a predetermined time based on a design rule used to calculate pulse duration, the design rule calculating the pulse duration to correspond to substantially the peak response of the patient's heart-cell membrane to the first-phase pulse component.

16. The method of claim 15, further comprising:
   (c) applying the waveform to the chest of a patient.

17. The method of claim 15, wherein the waveform is biphasic.

18. The method of claim 17, wherein step (b) includes generating an emulated second-phase substantially sinusoidally shaped pulse component having a second polarity.

19. The method of claim 15, further comprising:
   (c) sequentially interconnecting the capacitors in a circuit with one another to generate a second phase of a waveform.

20. Apparatus for generating a waveform, the waveform for use in externally defibrillating the heart of a patient, the apparatus comprising:
   a plurality of capacitors, the plurality of capacitors being chargeable to respective charge potentials by at least one charging device operably coupled to the plurality of capacitors; and
   control apparatus operatively coupled with the capacitors to sequentially interconnect the capacitors in a circuit with one another to generate a waveform, the waveform comprising an emulated first-phase substantially sinusoidally shaped pulse component having a first polarity, the control apparatus being constructed to truncate the emulated first-phase pulse component at a predetermined time based on a design rule used to calculate pulse duration, the design rule calculating the pulse duration to correspond to substantially the peak response of the patient's heart-cell membrane to the first-phase pulse component.

21. Apparatus for generating a waveform, the waveform for use in externally defibrillating the heart of a patient, the apparatus comprising:

capacitor means for being charged to respective charge potentials, the capacitor means comprising a plurality of elements; and control means operatively coupled with the capacitor means for sequentially interconnecting a plurality of the elements of the capacitor means in a circuit with one another to generate a waveform, the waveform comprising an emulated first-phase substantially sinusoidally shaped pulse component having a first polarity, the control means truncating the emulated first-phase pulse component at a predetermined duration, the design rule used to calculate pulse duration, the design rule calculating the pulse duration to correspond to substantially the peak response of the patient's heart-cell membrane to the first-phase component.

22. A method of generating a waveform for use in externally defibrillating the heart of a patient, the method comprising:

(a) charging a plurality of capacitors to charge potentials; and (b) sequentially interconnecting the capacitors in a circuit with one another to generate a waveform;

wherein step (b) includes generating a first-phase sinusoidally shaped pulse component having a first polarity and truncating the emulated first-phase pulse component at a predetermined time based on a design rule used to calculate pulse duration, the design rule calculating the pulse duration to correspond to substantially the peak response of the patient's heart-cell membrane to the first-phase pulse component.

* * * * *